(12) United States Patent
Bache et al.

(10) Patent No.: US 10,993,819 B2
(45) Date of Patent: *May 4, 2021

(54) ADJUSTABLE SOCKET SYSTEM

(71) Applicant: OSSUR ICELAND EHF, Reykjavik (IS)

(72) Inventors: Andrew Bache, Reykjavik (IS); Martin Lund Storup, Reykjavik (IS); Alexander Johonnuson, Kopavogur (IS); Andri Orrason, Reykjavik (IS); Gudmundur Karason, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 356 days.

This patent is subject to a terminal disclaimer.

(21) Appl. No.: 15/888,403

(22) Filed: Feb. 5, 2018

(65) Prior Publication Data

US 2018/0221179 A1 Aug. 9, 2018

Related U.S. Application Data

(60) Provisional application No. 62/455,133, filed on Feb. 6, 2017, provisional application No. 62/458,170, filed (Continued)

(51) Int. Cl.
*A61F 2/80* (2006.01)
*A61F 2/78* (2006.01)
(Continued)

(52) U.S. Cl.
CPC .................. *A61F 2/80* (2013.01); *A61F 2/76* (2013.01); *A61F 2/78* (2013.01); *A61F 2/7812* (2013.01);
(Continued)

(58) Field of Classification Search
CPC ........................................................ A61F 2/80
(Continued)

(56) References Cited

U.S. PATENT DOCUMENTS

| 37,282 A | 1/1863 | Engelbrecht et al. |
|---|---|---|
| 51,593 A | 12/1865 | Jewett |

(Continued)

FOREIGN PATENT DOCUMENTS

| CA | 2854799 A1 | 5/2013 |
|---|---|---|
| CA | 2889617 A1 | 5/2014 |

(Continued)

OTHER PUBLICATIONS

International Search Report from PCT Application No. PCT/US2019/036267, dated Sep. 30, 2019.

(Continued)

*Primary Examiner* — David H Willse
(74) *Attorney, Agent, or Firm* — Workman Nydegger

(57) ABSTRACT

An adjustable socket system includes a plurality of shell components and longitudinal supports connected to a base and is movable between an open configuration to loosen the fit of the adjustable socket system, and a closed configuration to secure the fit of the adjustable socket system on residual limb received therein. A tightening system includes a tensioning unit having a handle defining a moment arm rotatable about a rotation axis, and a tensioning element operatively coupled to the handle via a movable connection point and to the shell components via a control point. Rotation of the handle displaces the movable connection point and the tensioning element relative to the control point to move the adjustable socket system to the closed configuration.

16 Claims, 9 Drawing Sheets

Related U.S. Application Data on Feb. 13, 2017, provisional application No. 62/597,113, filed on Dec. 11, 2017.

(51) Int. Cl.
*A61F 2/76* (2006.01)
*A61F 2/50* (2006.01)

(52) U.S. Cl.
CPC . *A61F 2002/502* (2013.01); *A61F 2002/5007* (2013.01); *A61F 2002/5018* (2013.01); *A61F 2002/5026* (2013.01); *A61F 2002/5038* (2013.01); *A61F 2002/5083* (2013.01); *A61F 2002/5084* (2013.01); *A61F 2002/5092* (2013.01); *A61F 2002/5093* (2013.01); *A61F 2002/7625* (2013.01)

(58) Field of Classification Search
USPC .......................................................... 623/33
See application file for complete search history.

(56) References Cited

U.S. PATENT DOCUMENTS

| | | |
|---|---|---|
| 366,494 A | 7/1887 | Marks |
| 470,431 A | 3/1892 | Marks |
| 1,066,605 A | 7/1913 | Hanger |
| 1,082,256 A | 12/1913 | Apgar |
| 1,144,681 A | 6/1915 | Apgar |
| 1,861,311 A | 5/1932 | Logan |
| 1,893,853 A | 1/1933 | Tullis |
| 2,025,835 A | 12/1935 | Trautman |
| 2,229,728 A | 1/1941 | Eddels |
| 2,634,424 A | 4/1953 | O'Gorman |
| 2,669,728 A | 2/1954 | Ritchie |
| 2,759,271 A | 8/1956 | Von Duyke |
| 2,908,016 A | 10/1959 | Botko |
| 2,949,674 A | 8/1960 | Wexler |
| 3,678,587 A | 7/1972 | Madden |
| 4,128,903 A | 12/1978 | Marsh et al. |
| 4,161,042 A | 7/1979 | Cottingham et al. |
| 4,225,982 A | 10/1980 | Cochrane et al. |
| 4,268,922 A * | 5/1981 | Marsh ............. A61F 2/60 623/27 |
| 4,283,800 A | 8/1981 | Wilson |
| 4,300,245 A | 11/1981 | Saunders |
| 4,459,709 A | 7/1984 | Leal et al. |
| 4,704,129 A | 11/1987 | Massey |
| 4,715,124 A | 12/1987 | Harrington |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,938,775 A | 7/1990 | Morgan |
| 4,988,360 A | 1/1991 | Shamp |
| 5,003,969 A | 4/1991 | Azer et al. |
| 5,014,441 A | 5/1991 | Pratt |
| 5,108,456 A | 4/1992 | Coonan, III |
| 5,133,777 A | 7/1992 | Arbogast et al. |
| 5,168,635 A | 12/1992 | Hoffman |
| 5,201,773 A | 4/1993 | Carideo, Jr. |
| 5,201,775 A | 4/1993 | Arbogast et al. |
| 5,246,464 A | 9/1993 | Sabolich |
| 5,312,669 A | 5/1994 | Bedard |
| 5,424,782 A | 6/1995 | Aoki |
| 5,503,543 A | 4/1996 | Laghi |
| 5,520,529 A | 5/1996 | Heckel |
| 5,529,575 A | 6/1996 | Klotz |
| 5,529,576 A | 6/1996 | Lundt et al. |
| 5,545,231 A | 8/1996 | Houser |
| 5,571,209 A | 11/1996 | Brown, Sr. |
| 5,651,792 A | 7/1997 | Telikicherla |
| 5,652,053 A | 7/1997 | Liegeois |
| 5,653,766 A | 8/1997 | Naser |
| 5,718,925 A | 2/1998 | Kristinsson et al. |
| 5,724,714 A | 3/1998 | Love |
| 5,728,165 A | 3/1998 | Brown, Sr. |
| 5,800,565 A | 9/1998 | Biedermann |
| 5,824,111 A | 10/1998 | Schall et al. |
| 5,885,509 A | 3/1999 | Kristinsson |
| 5,888,215 A | 3/1999 | Roos et al. |
| 5,888,217 A | 3/1999 | Slemker |
| 5,867,517 A | 4/1999 | Laghi |
| 6,033,440 A | 3/2000 | Schall et al. |
| 6,051,026 A | 4/2000 | Biedermann et al. |
| 6,077,300 A | 6/2000 | Sabolich et al. |
| 6,206,932 B1 | 3/2001 | Johnson |
| 6,228,124 B1 | 5/2001 | Slemker et al. |
| 6,231,618 B1 | 5/2001 | Schall et al. |
| 6,238,437 B1 | 5/2001 | Johnson et al. |
| 6,334,876 B1 | 1/2002 | Perkins |
| 6,368,357 B1 | 4/2002 | Schon et al. |
| 6,406,499 B1 | 6/2002 | Kania |
| 6,444,282 B1 | 9/2002 | Shirer |
| 6,458,163 B1 | 10/2002 | Slemker et al. |
| 6,497,028 B1 | 12/2002 | Rothschild et al. |
| 6,500,210 B1 | 12/2002 | Sabolich et al. |
| 6,557,177 B2 | 5/2003 | Hochmuth |
| 6,669,736 B2 | 12/2003 | Slemker et al. |
| 6,700,563 B1 | 3/2004 | Koizumi |
| 6,761,743 B1 | 7/2004 | Johnson |
| 6,793,682 B1 | 9/2004 | Mantelmacher |
| 6,942,703 B2 | 9/2005 | Carstens |
| 6,974,484 B2 | 12/2005 | Caspers |
| 6,991,657 B1 | 1/2006 | Price, Jr. |
| 7,090,700 B2 | 8/2006 | Curtis |
| 7,094,212 B2 | 8/2006 | Karason et al. |
| 7,097,799 B1 | 8/2006 | Burton |
| 7,105,122 B2 | 9/2006 | Karason |
| 7,118,602 B2 | 10/2006 | Bjarnason |
| 7,172,714 B2 | 2/2007 | Jacobson |
| 7,240,414 B2 | 7/2007 | Taylor, Sr. |
| 7,288,116 B2 | 10/2007 | Ikeda |
| 7,300,466 B1 | 11/2007 | Martin |
| 7,318,504 B2 | 1/2008 | Vitale et al. |
| 7,338,532 B2 | 3/2008 | Haberman et al. |
| 7,344,567 B2 | 3/2008 | Slemker |
| 7,402,265 B2 | 7/2008 | Jacobson |
| 7,479,163 B2 | 1/2009 | Slemker et al. |
| 7,488,349 B2 | 2/2009 | Einarsson |
| 7,591,857 B2 | 9/2009 | Slemker et al. |
| 7,658,720 B2 | 2/2010 | Johnson, III |
| 7,727,284 B2 | 6/2010 | Warila |
| 7,753,866 B2 | 7/2010 | Jackovitch |
| 7,762,973 B2 | 7/2010 | Einarsson et al. |
| 7,867,286 B2 | 1/2011 | Einarsson |
| 7,980,921 B2 | 7/2011 | Saravanos |
| 7,985,192 B2 | 7/2011 | Sheehan et al. |
| 8,007,544 B2 | 8/2011 | Jonsson et al. |
| 8,083,807 B2 | 12/2011 | Auberger et al. |
| 8,088,320 B1 | 1/2012 | Bedard |
| 8,116,900 B2 | 2/2012 | Slemker et al. |
| 8,123,818 B2 | 2/2012 | Bjarnason et al. |
| 8,142,517 B2 | 3/2012 | Horie |
| 8,303,527 B2 | 11/2012 | Joseph |
| 8,308,815 B2 | 11/2012 | McCarthy |
| 8,323,353 B1 | 12/2012 | Alley et al. |
| 8,382,852 B2 | 2/2013 | Laghi |
| 8,403,993 B2 | 3/2013 | Aram et al. |
| 8,414,658 B2 | 4/2013 | Johnson et al. |
| 8,470,050 B2 | 6/2013 | Dillingham |
| 8,480,758 B2 | 7/2013 | McLeod |
| 8,491,667 B2 | 7/2013 | Dillingham |
| 8,535,389 B2 | 9/2013 | McKinney |
| 8,576,250 B2 | 11/2013 | Sabiston et al. |
| 8,656,918 B1 | 2/2014 | Alley et al. |
| 8,795,385 B2 | 8/2014 | Bache |
| 8,845,755 B2 | 9/2014 | Dillingham |
| 8,978,224 B2 | 3/2015 | Hurley et al. |
| 9,044,349 B2 | 6/2015 | Hurley et al. |
| 9,050,202 B2 | 6/2015 | Bache et al. |
| 9,248,033 B2 | 2/2016 | Bache |
| 9,283,093 B2 | 3/2016 | Alley |
| 9,468,542 B2 | 10/2016 | Hurley et al. |

(56) References Cited

U.S. PATENT DOCUMENTS

| | | |
|---|---|---|
| 9,468,543 B2 | 10/2016 | Hurley et al. |
| 9,474,633 B2 | 10/2016 | Williams et al. |
| 9,504,585 B2 | 11/2016 | Cornell |
| 9,549,828 B2 | 1/2017 | Hurley et al. |
| D778,452 S | 2/2017 | Cespedes et al. |
| 9,572,691 B2 | 2/2017 | Pacanowsky et al. |
| 10,172,728 B2 | 1/2019 | Hurley et al. |
| 10,179,056 B2 | 1/2019 | Hurley et al. |
| 10,206,795 B2 | 2/2019 | Pedtke et al. |
| 2002/0099450 A1 | 7/2002 | Dean, Jr. et al. |
| 2003/0181990 A1 | 9/2003 | Phillips |
| 2004/0260402 A1 | 12/2004 | Baldini et al. |
| 2005/0209706 A1 | 9/2005 | Warila |
| 2005/0216096 A1 | 9/2005 | Wagman |
| 2005/0267600 A1 | 12/2005 | Haberman et al. |
| 2005/0278039 A1 | 12/2005 | Nobbe |
| 2005/0288798 A1 | 12/2005 | Curtis |
| 2006/0009860 A1 | 1/2006 | Price, Jr. |
| 2006/0020348 A1 | 1/2006 | Slemker et al. |
| 2006/0135902 A1 | 6/2006 | Ingimundarson et al. |
| 2007/0004993 A1 | 1/2007 | Coppens et al. |
| 2007/0078523 A1 | 4/2007 | Kholwadwala et al. |
| 2007/0152379 A1 | 7/2007 | Jacobson |
| 2007/0298075 A1 | 12/2007 | Borgia et al. |
| 2008/0066272 A1 | 3/2008 | Hammerslag et al. |
| 2008/0269914 A1 | 10/2008 | Coppens et al. |
| 2009/0036999 A1 | 2/2009 | Egilsson et al. |
| 2009/0076625 A1 | 3/2009 | Groves et al. |
| 2009/0105844 A1 | 4/2009 | Ortiz |
| 2009/0240344 A1 | 9/2009 | Colvin et al. |
| 2009/0287128 A1 | 11/2009 | Ingimundarson et al. |
| 2009/0299490 A1 | 12/2009 | Summit |
| 2010/0030344 A1 | 2/2010 | Hansen |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0121464 A1 | 5/2010 | Mantelmacher |
| 2010/0160722 A1 | 6/2010 | Kuyava et al. |
| 2010/0191348 A1* | 7/2010 | Kettwig ............... A61F 2/78 623/33 |
| 2010/0274364 A1 | 10/2010 | Pacanowsky et al. |
| 2011/0029096 A1 | 2/2011 | Laghi |
| 2011/0035027 A1 | 2/2011 | McCarthy |
| 2011/0071647 A1* | 3/2011 | Mahon ............... A61F 2/5046 623/33 |
| 2011/0114635 A1 | 5/2011 | Sheehan |
| 2011/0232837 A9 | 9/2011 | Ottleben |
| 2011/0320010 A1 | 12/2011 | Vo |
| 2012/0022667 A1 | 1/2012 | Accinni et al. |
| 2012/0041567 A1 | 2/2012 | Cornell |
| 2012/0095570 A1 | 4/2012 | Marquette |
| 2012/0101417 A1 | 4/2012 | Joseph |
| 2012/0101597 A1 | 4/2012 | Bache |
| 2012/0143077 A1 | 6/2012 | Sanders et al. |
| 2012/0165956 A1 | 6/2012 | Li |
| 2012/0191218 A1 | 7/2012 | McCarthy |
| 2012/0215324 A1 | 8/2012 | King |
| 2012/0253475 A1 | 10/2012 | Kelley et al. |
| 2012/0259432 A1 | 10/2012 | Dillingham |
| 2012/0259434 A1 | 10/2012 | Dillingham |
| 2012/0271210 A1 | 10/2012 | Galea et al. |
| 2012/0271433 A1 | 10/2012 | Galea et al. |
| 2012/0283846 A1 | 11/2012 | Janssen et al. |
| 2012/0293411 A1 | 11/2012 | Eithinger et al. |
| 2013/0123940 A1 | 5/2013 | Hurley et al. |
| 2013/0192071 A1 | 8/2013 | Esposito et al. |
| 2013/0197318 A1 | 8/2013 | Herr et al. |
| 2013/0218296 A1 | 8/2013 | Koniuk et al. |
| 2013/0245785 A1 | 9/2013 | Accini et al. |
| 2013/0282141 A1 | 10/2013 | Herr et al. |
| 2014/0031953 A1 | 1/2014 | Mackenzie |
| 2014/0121783 A1 | 5/2014 | Alley |
| 2014/0135946 A1 | 5/2014 | Hurley et al. |
| 2014/0149082 A1 | 5/2014 | Sanders et al. |
| 2014/0227584 A1 | 9/2014 | Hurley et al. |
| 2014/0277585 A1 | 9/2014 | Kelley et al. |
| 2015/0018974 A1 | 1/2015 | Dillingham |
| 2015/0105867 A1 | 4/2015 | Novak |
| 2015/0168943 A1 | 6/2015 | Hurley et al. |
| 2015/0190252 A1 | 6/2015 | Hurley et al. |
| 2015/0230945 A1 | 8/2015 | Bache et al. |
| 2015/0257905 A1 | 9/2015 | Bache |
| 2015/0265434 A1 | 9/2015 | Hurley et al. |
| 2015/0313729 A1 | 11/2015 | Williams et al. |
| 2015/0313730 A1 | 11/2015 | Hurley et al. |
| 2015/0352775 A1 | 12/2015 | Geshlider et al. |
| 2016/0000586 A1 | 1/2016 | Hurley et al. |
| 2016/0000587 A1 | 1/2016 | Hurley et al. |
| 2016/0058584 A1 | 3/2016 | Cespedes et al. |
| 2016/0143752 A1 | 5/2016 | Hurley et al. |
| 2016/0158035 A1 | 6/2016 | Alley |
| 2016/0235560 A1 | 8/2016 | Cespedes et al. |
| 2016/0278949 A1 | 9/2016 | Dillingham |
| 2016/0331562 A1 | 11/2016 | Bache et al. |
| 2016/0334780 A1 | 11/2016 | Dair et al. |
| 2016/0338858 A1 | 11/2016 | Hurley et al. |
| 2017/0027718 A1 | 2/2017 | Williams et al. |
| 2017/0128238 A1 | 5/2017 | Hurley et al. |
| 2017/0156896 A1 | 6/2017 | Alley |
| 2018/0000615 A1 | 1/2018 | Hurley et al. |
| 2018/0008434 A1 | 1/2018 | Geiger et al. |
| 2018/0020973 A1 | 1/2018 | Hurley et al. |
| 2018/0021153 A1 | 1/2018 | Hurley et al. |
| 2018/0153716 A1 | 6/2018 | Martin |
| 2018/0221178 A1 | 8/2018 | Steinberg et al. |
| 2018/0263702 A1 | 9/2018 | Hurley et al. |
| 2018/0296373 A1 | 10/2018 | Granz |
| 2018/0303637 A1 | 10/2018 | Bache et al. |
| 2018/0333279 A1 | 11/2018 | Granz et al. |

FOREIGN PATENT DOCUMENTS

| | | |
|---|---|---|
| CN | 104884005 A | 9/2015 |
| CN | 104053416 B | 11/2016 |
| CN | 106913407 A | 7/2017 |
| CN | 109328045 A | 2/2019 |
| DE | 319623 C | 3/1920 |
| DE | 19529055 A1 | 1/1997 |
| DE | 102014001000 A1 | 7/2014 |
| EP | 0204407 A2 | 12/1986 |
| EP | 0269391 A2 | 6/1998 |
| EP | 1433447 A2 | 6/2004 |
| EP | 1656911 A1 | 5/2006 |
| EP | 2866747 B1 | 2/2017 |
| GB | 127 451 A | 6/1919 |
| GB | 675811 A | 7/1952 |
| GB | 2080114 A | 2/1982 |
| GB | 2169207 A | 7/1986 |
| RU | 2088182 C1 | 8/1997 |
| WO | 91/16019 A1 | 10/1991 |
| WO | 98/12994 A1 | 4/1998 |
| WO | 0003665 A1 | 1/2000 |
| WO | 0030572 A1 | 6/2000 |
| WO | 2007/035875 A2 | 3/2007 |
| WO | 2008/116025 A2 | 9/2008 |
| WO | 2009/093020 A2 | 7/2009 |
| WO | 2012/021823 A1 | 2/2012 |
| WO | 2012054700 A1 | 4/2012 |
| WO | 2013/071308 A1 | 5/2013 |
| WO | 2014004709 A1 | 1/2014 |
| WO | 2014005071 A1 | 1/2014 |
| WO | 2014068269 A1 | 5/2014 |
| WO | 2014070666 A1 | 5/2014 |
| WO | 2014153244 A1 | 9/2014 |
| WO | 2014205403 A1 | 12/2014 |
| WO | 2015095232 A1 | 6/2015 |
| WO | 2015143249 A1 | 9/2015 |
| WO | 2016183065 A1 | 11/2016 |
| WO | 2017186901 A1 | 11/2017 |
| WO | 2017186902 A1 | 11/2017 |

(56) References Cited

FOREIGN PATENT DOCUMENTS

| | | | |
|---|---|---|---|
| WO | 2017194479 A1 | 11/2017 | |
| WO | 2018017959 A1 | 1/2018 | |

OTHER PUBLICATIONS

Initial and Interim Prostheses [Retrieved from Internet on Feb. 11, 2013], <URL:http://www.ottobockus.com/cps/rde/xbcr/ob_us_en/08cat_4.pdf>. Published in Prosthetics Lower Extremities 2008, see contents page <URL:http://www.ottobockus.com/cps/rde/xbcr/ob_us_en/08cat_1.pdf> pp. 24-31.

Manual: "Socket Evaluation System with the Rapid Adjustment Pylon", [retrieved from the internet on May 22, 2014], <URL:http://www.fillauer.com>; 4 pages.

Alley, "The High-Fidelity Interface: Skeletal Stabilization Through Alternating Soft Tissue Compression and Release" Proceedings of the 2011 MyoElectric Controls/Powered Prosthetics Symposium Frederiction, New Brunswick, Canada, Aug. 2011. 3 Pages.

Andrysek, "Lower-Limb Prosthetic Technologies in the Developing World: A Review of Literature from 1994-2010", Prosthetics and Orthotics International, Cardiff, Wales, UK; vol. 34, No. 4, Dec. 2010; pp. 378-398.

Conn, "Materials Science: A Look At Some of the Substances on the Market for Device Fabrication", O&P Almanac, Jun. 2012, pp. 28-31; http://wwww.allardusa.com/pdf/articles/Materials%20Science%20Article%20-%20June% 202012%20O%26P%20Almanac.pdf.

Fairley, M. "From Academia to the Developing World: Student Engineers Create Collaborative Technologies", The O&P Edge Magazine, OandP.com, Mar. 2011, pp. 1-9. Downloaded from http://www.oandp.com/articles/2011-05-03.asp.

Fairley, M. "M.A.S. Socket: A Transfemoral Revolution", The O&P Edge, Jun. 2004, www.oandp.com/articles/2004-06_03.asp. 5 Pages.

"COMFIL—Thermo Formable Composite Technique", Fillaur LLC and Centri, Fabrication Manuel, Jun. 15, 2012, pp. 1-13.

Gard, S.A. "Overview of Lower Limb Prosthetics Research", WRAMC and the VA Orthopedic & Prosthetic Workshop Arlington, VA, Nov. 17-18, 2003, pp. 1-49.

Geil, M.D., "Consistency, Precision, and Accuracy of Optical and Electromagnetic Shape-Capturing Systems for Digital Measurement of Residual-limb Anthropometrics of Persons With Transtibial Amputation", Journal of Rehabilitation Research and Development, vol. 44, No. 4, 2007; pp. 515-524.

Gleave, "A Plastic Socket and Stump Casting Technique for Above-Knee Prostheses", Orthopaedic and Prosthetic Appliance Department, Hong Kong Government Medical Department, The Journal of Bone and Joint Surgery, vol. 47B, No. 1, Feb. 1965, pp. 100-103.

Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. 1 page.

Greenwald, et al., "Volume Management: Smart Variable Geometry Socket (SVGS) Technology for Lower-Limb Prostheses", American Academy of Orthotists & Prosthetists, vol. 15, No. 3, 2003, pp. 107-112.

Hong, et al, "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. 1 Page.

Hwang, "Blooming Winner—Spark!", Spark Galleries, 2012/Spark/Concept,Spark Design Awards, 2012 3 Pages. Downloaded from http://www.sparkawards.com/galleriew/index.cfm?entry=9525D900-EoEF-59BD-46597D99 . . . .

Jana, "Designing a Cheaper, Simpler Prosthetic Arm", ZDNet, Nov. 14, 2011, pp. 1-5. Downloaded from http://www.2dnet.com/article/designing-a-cheaper-simpler-prosthetic-arm/.

Koike, et al., "The TC Double Socket Above-knee Prosthesis", Prosthetics and Orthotics International, vol. 5, 1981 pp. 129-134.

Krouskop, et al., "Computer-aided design of a prosthetic socket for an above-knee amputee", Journal of Rehabilitation Research and Development, vol. 24, No. 2 1987, pp. 31-38.

Manucharian, "An Investigation of Comfort Level Trend Differences Between the Hands-On Patellar Tendon Bearing and Hands-Off Hydrocast Transtibial Prosthetic Sockets", JPO: American academy of Orthotists & Prosthetists, Washington, D.C., U.S.A.; vol. 23, No. 3, 2011: pp. 124-140.

Otto Bock Healthcare LLP, "Initial and Interim Prostheses", Otto Bock Healthcare LLP, Prosthetics Lower Extremities 2008, Feb. 2013 pp. 1-8, www.ottobockus.com/cps/rde/xbcr/ob_us_en/08cat_1.pdf.

Otto Bock Healthcare LLP , "Ottobock: PU Resin Kit Polytol"; Downloaded Dec. 17, 2012 from http://www.ottobock.com/cps/rde/xchg/ob_com_en/hs.xs1/17414.html.

Sanders, et al., "Residual limb volume change: Systematic review of measurement and management", Journal of Rehabilitation Research & Development, 2011, vol. 48, No. 8, pp. 949-986.

Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 27, No. 1; pp. 71-74.

SBIR topic summary: "Pro-Active Dynamic Accommodating Socket", http://www.dodsbir.net/sitis/archieves_display_topic.asp?Bookmark=34570; downloaded Mar. 25, 2013, U.S. A. 3 pages.

Smith, "Silver Linings for O&P Devices", The Academy Today, vol. 1, No. 4: Oct. 2005, 4 Pages, Downloaded from, http://wwww.oandp.org/AcademyTODAY/20050ct/7.asp.

Spaeth, JP , "Laser Imaging and Computer-Aided Design and Computer-Aided Manufacture in Prosthetics and Orthotics", Physical Medicine and Rehabilitation Clinics of North America, Elsevier Publishing, Amsterdam, The Netherlands; Feb. 2006 pp. 245-263, Abstract. 2 pages.

Turner, "FIT for Everyone", Yanko Design-Form Beyond Junction, Jul. 17, 2015, pp. 1-10. Downloaded from http://www.yankodesign.com/2013/07/17/fit-for-erveryone/.

"Hanger ComfortFlex Socket System for Prosthetic Devices:" Downloaded Nov. 28, 2012 from http://www.hanger.com/prosthetics/services/Technology/Pages/ComfortFlex.asp pp. 1-2.

Wilson Jr. "A Material for Direct Forming of Prosthetic Sockets", Artificial Limbs., vol. 4, No. 1, 1970, Downloaded from http://www.oandplibrary.org/al/1970_01_053.asp; downloaded Dec. 14, 2012. pp. 53-56.

Wilson, "Recent Advances in Above-Knee Prosthetics", Artificial Limbs, vol. 12, No. 2, 1968 pp. 1-27.

Wu, et al, "CIR sand casting system for trans-tibial socket", Prosthetics and Orthotics International, Aug. 2003: vol. 27, pp. 146-152.

Quigley, Michael, "Prosthetic Management: Overview, Methods and Materials," Chapter 4, Atlas of Limb Prosthetics: Surgical, Prosthetic, and Rehabilitation Principles, Second Edition, 1992, 10 Pages. Downloaded from: http://www.oandplibrary.org/alp/chapot-01.asp.

Burgess, et al. "Immediate Post-Surgical Prosthetic Fitting", The Management of Lower-Extremity Amputations, Aug. 1969, pp. 42-51.

Compton, et al., "New Plastics for Forming Directly on the Patient", Prosthetics and Orthotics International, 1978, vol. 2, No. 1, pp. 43-47, Abstract. 3 Pages.

Fairley, "Socket Can Be Fabricated, Modified, Fitted—In One Hour", The O&P Edge, Jun. 2007. 5 Pages.

"Cut-4-Custom: Custom TLSO in Less Than an Hour", The O&P Edge, Oct. 2010. 2 Pages.

"Remoldable Prosthetics", InstaMorph Moldable Plastic, http://instamorph.com/wp-content/uploads/legcast1.png, Retrieved, May 10, 2016. 3 Pages.

International Search Report from PCT Application No. PCT/US2018/016802, dated May 2, 2018.

* cited by examiner

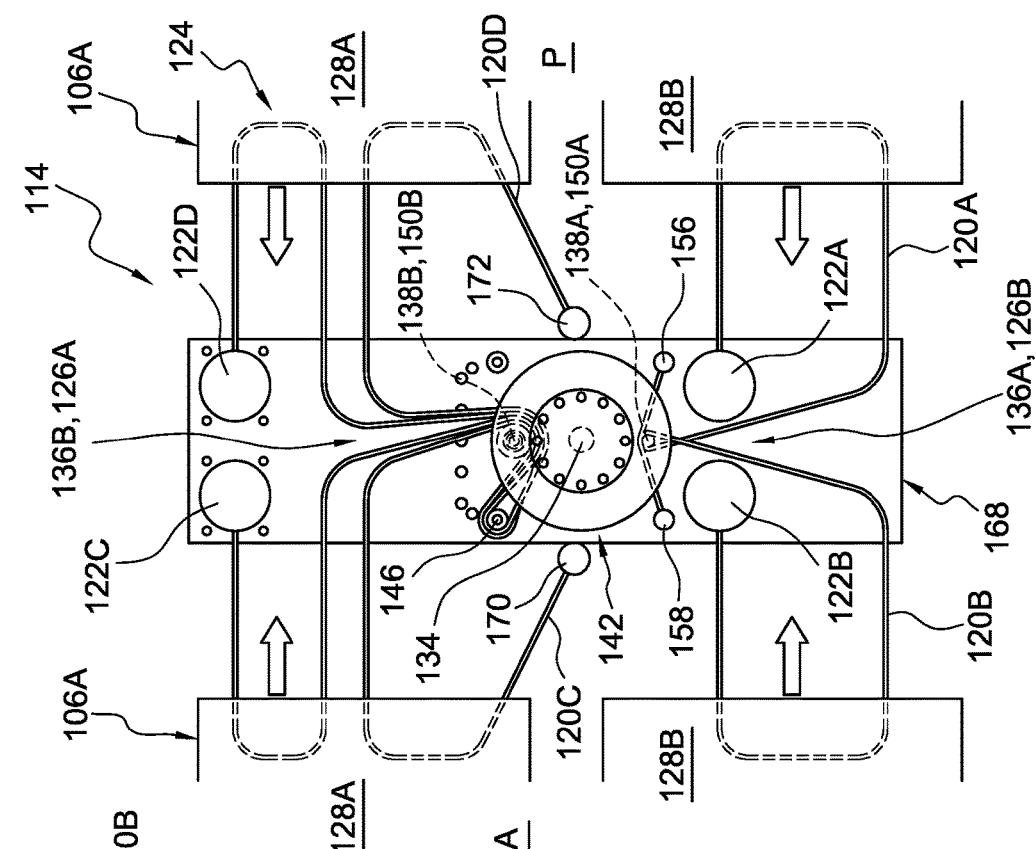
FIG. 6
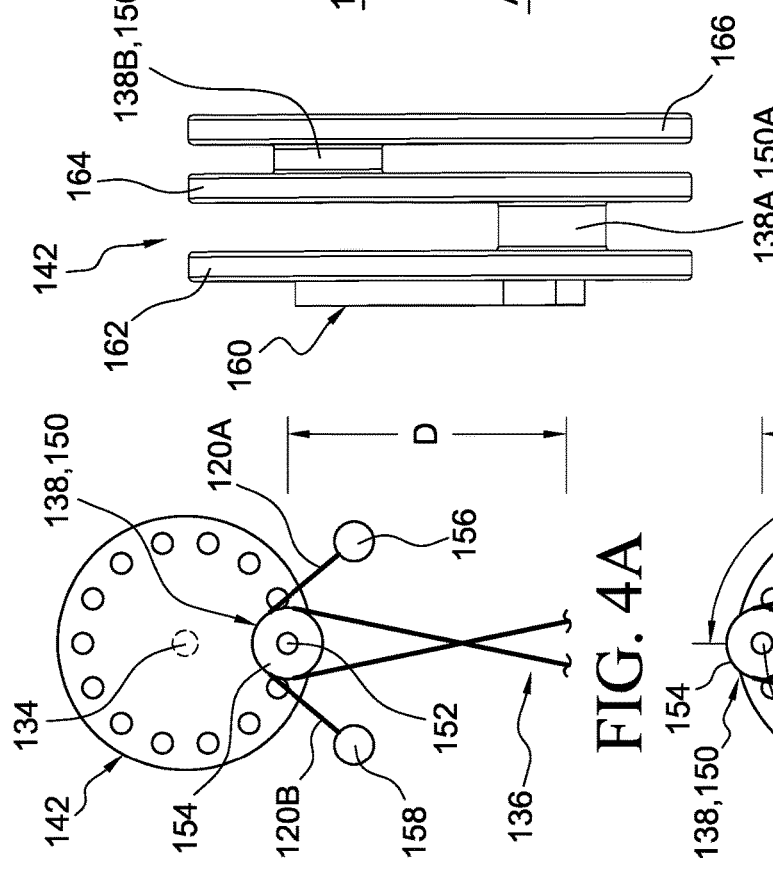
FIG. 5
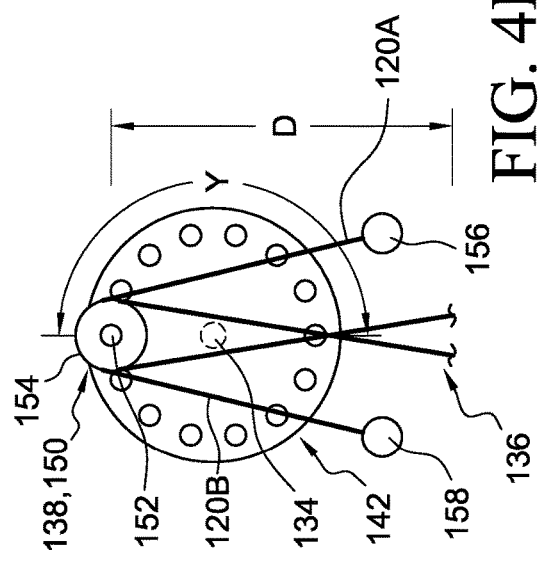
FIG. 4A
FIG. 4B

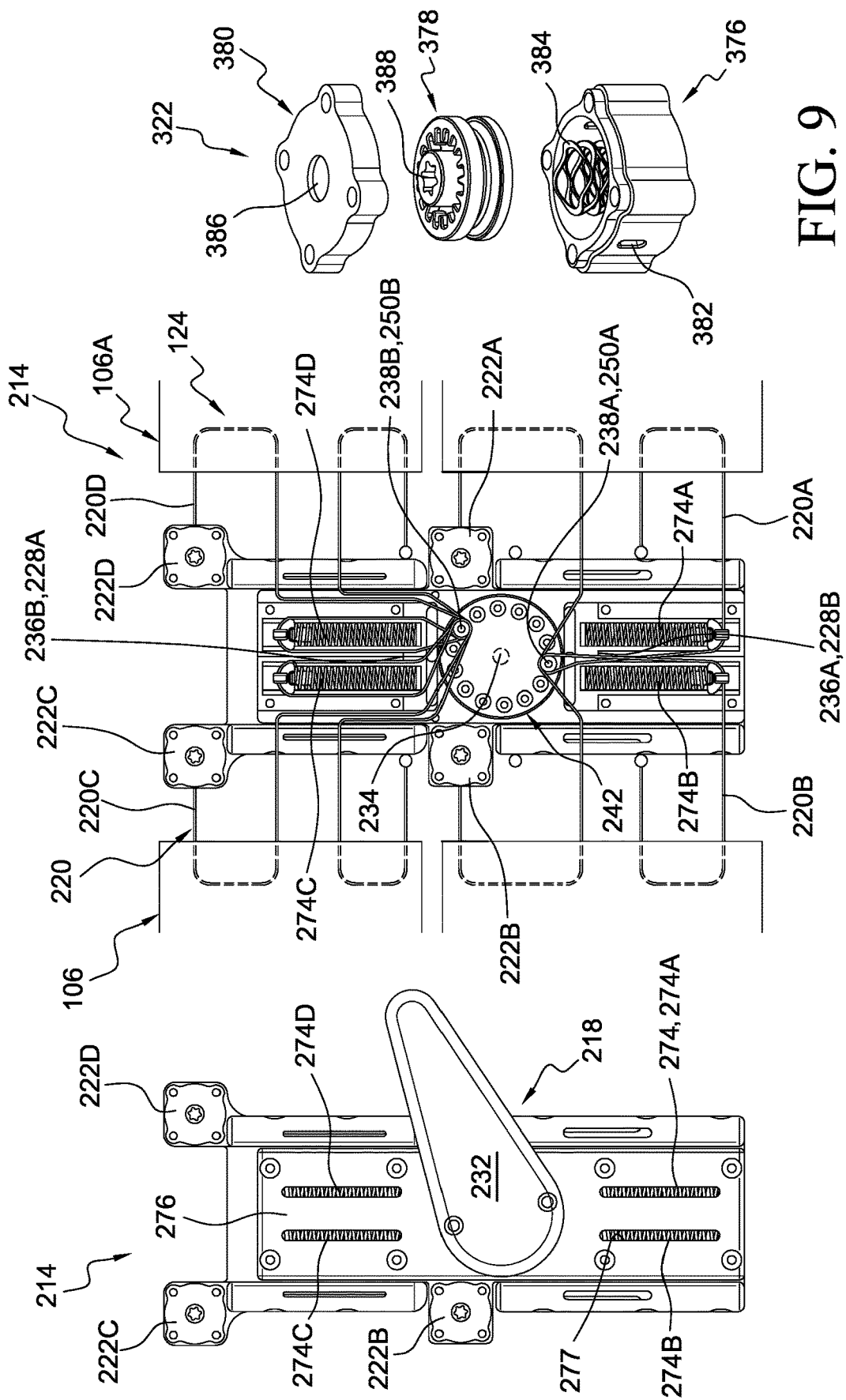

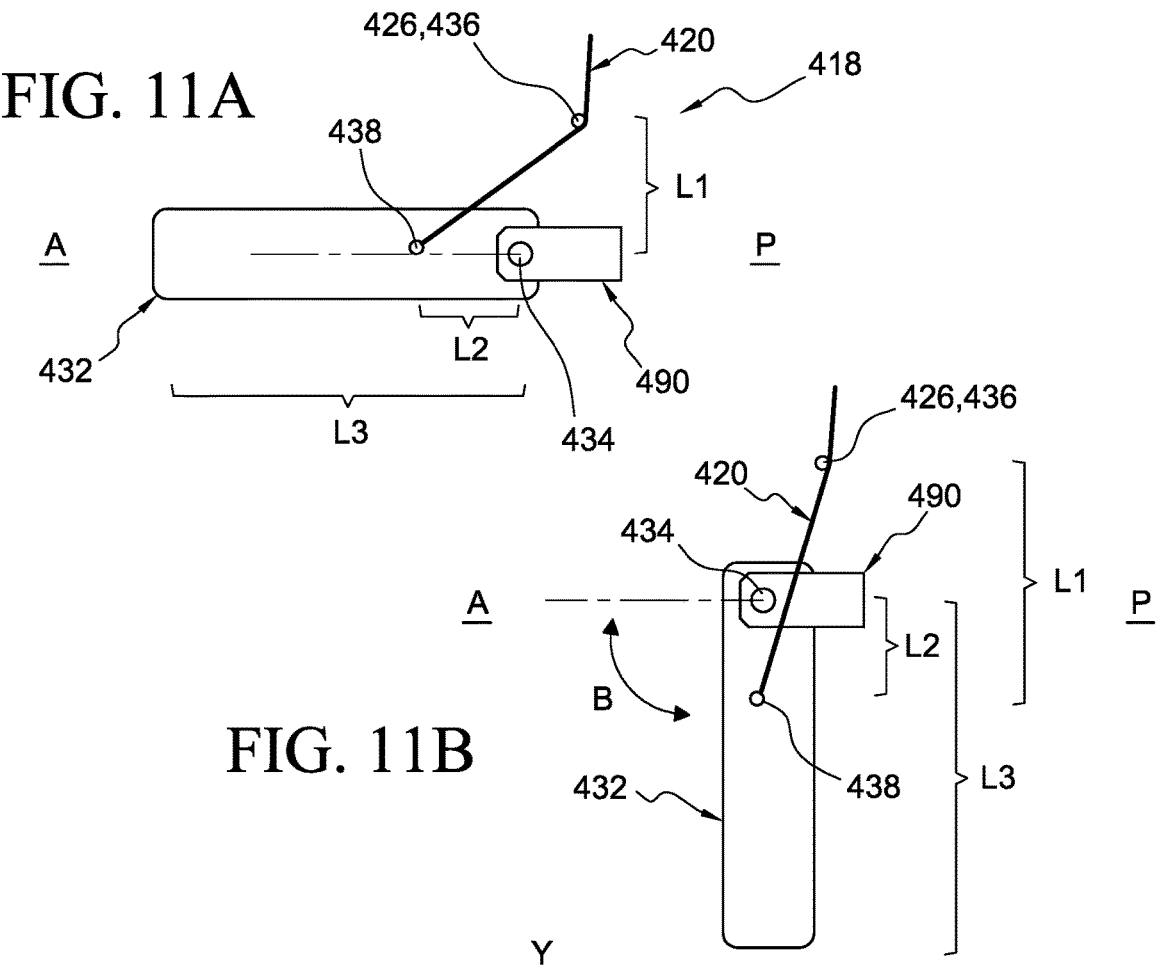
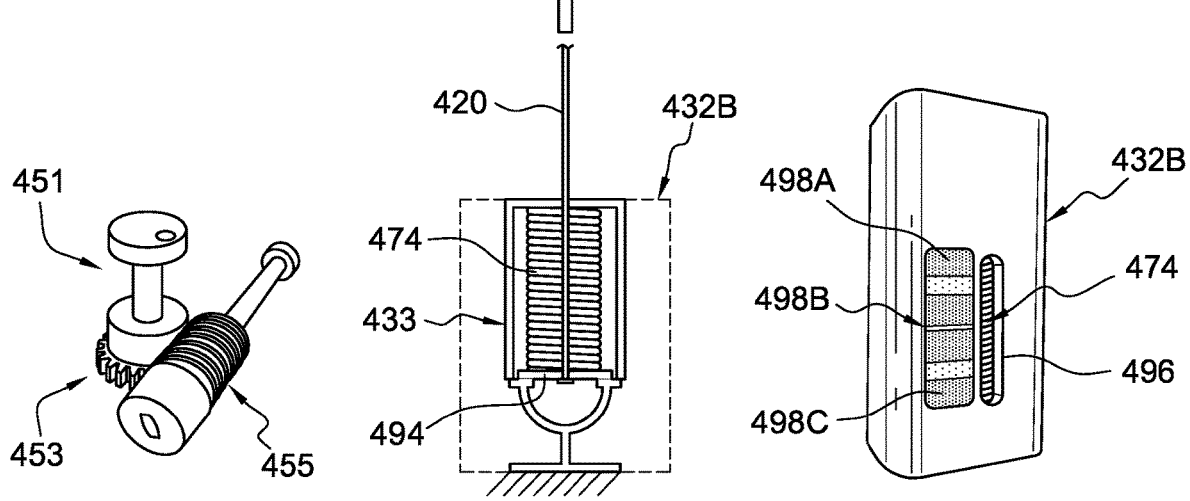
FIG. 12　FIG. 13　FIG. 14

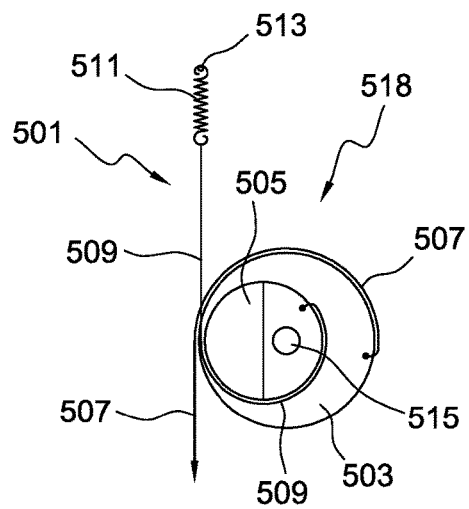 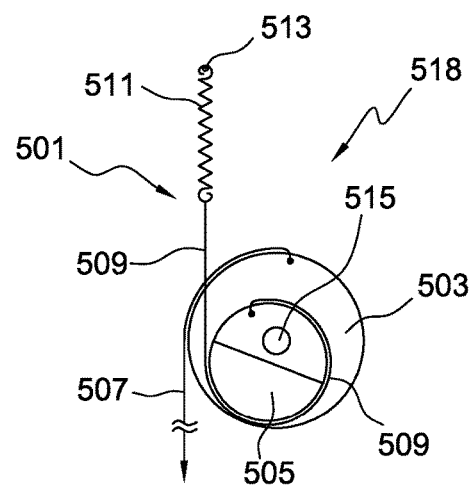
FIG. 15A     FIG. 15B
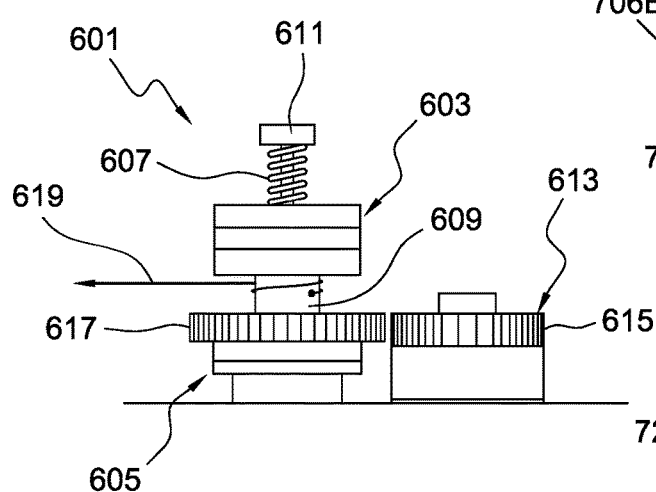
FIG. 16
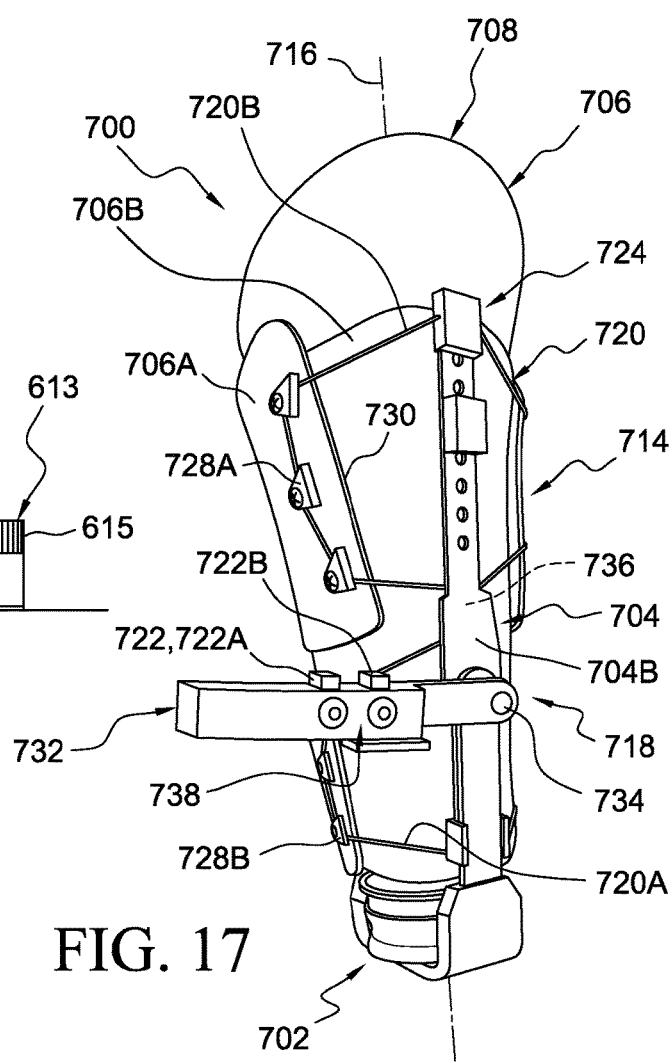
FIG. 17

ADJUSTABLE SOCKET SYSTEM

TECHNICAL FIELD

The disclosure relates to an adjustable socket system for a residual limb.

BACKGROUND

A typical prosthetic leg and foot includes a socket, pylon, and foot. A socket is commonly referred to as the portion of a prosthesis that fits around and envelops a residual limb or stump, and to which prosthetic components, such as a foot, are attached. Fitting and alignment of the socket are difficult tasks to perform, and require extensive knowledge, training and skill for the prosthetist.

The socket must fit closely to the stump to provide a firm connection and support, but must also be sufficiently loose to allow for circulation. In combination with proper fitting, the socket must transfer loads from the residual limb to the ground in a comfortable manner.

Conventional sockets are rigid and generally have a general uniform shape which receives a large portion of the residual limb. These sockets are permanently formed to a customized shape that is static, meaning the socket does not account for shape and volume fluctuations of the residual limb. When there are shape and volume fluctuations, the fitting of the socket is impeded, with these sockets causing discomfort, pain and soft tissue breakdown of the stump. Conventional sockets also tend to be bulky and cumbersome to wear, and may be difficult to don making the residual limb uncomfortable when worn.

Some attempts have been made to develop adjustable sockets with individual components that can be varied in size and/or shape to account for volume and shape fluctuations of the residual limb. These adjustable sockets however tend to have labor intensive and complicated tightening systems for donning and doffing the socket, making their use difficult for patients with limited dexterity, cognition, and/or strength. This can result in unsafe and improper use of the socket, causing discomfort and even injury.

In view of the foregoing, there is a need for an adjustable socket system that overcomes the problems of existing sockets.

SUMMARY

Embodiments of the present disclosure comprise an adjustable socket system that provide an intuitive and simple manner for users with limited dexterity or cognition to don and doff the system. From its straightforward and versatile design, the adjustable socket system can improve ease of use, and decrease the likelihood of over-tightening and/or under-tightening of the system over known adjustable socket systems.

An adjustable socket system of the present disclosure can include a base, a plurality of longitudinal supports connected to the base, and a plurality of shell components operatively connected to the longitudinal supports. The system is movable between an open configuration in which at least some of the shell components are moved radially outward relative to a longitudinal axis to loosen the fit of the system, and a closed configuration in which at least some of the shell components are moved radially inward relative to the open configuration to tighten the fit of the system or secure the fit of the system on the residual limb.

A tightening system is arranged to selectively move the adjustable socket system between the open and closed configurations. The tightening system includes a tensioning unit including at least one movable connection point and a handle defining a moment arm rotatable about a rotation axis, and at least one tensioning element operatively coupled to the handle via the at least one movable connection point and to at least one of the shell components via at least one control point. Rotation of the handle about the rotation axis from an off position to an on position displaces the at least one movable connection point and the at least one tensioning element relative to the at least one control point to tension the at least one tensioning element and move the adjustable socket system to the closed configuration.

Because the handle defines a moment, it provides a user a mechanical advantage, requiring less user strength to move the tensioning unit between the on position and the off position. In addition, the tensioning unit can have a binary configuration such that a user can only position and/or lock the handle in the on position or the off position, providing an intuitive and simple manner for users with limited dexterity or cognition to don and doff the adjustable socket system. This is beneficial over known tightening systems such as dial tensioners or strap systems which require complex levels of manual dexterity, making their use difficult and intimidating for many users. The binary configuration of the tensioning unit also allows the tensioning unit to control the basic fit of the adjustable socket system on the residual limb rather than requiring the user to precisely fit the system with straps or dial tensioners, as in the prior art, substantially decreasing the likelihood that a user will over-tighten or under-tighten the adjustable socket system, improving ease of use and safety (especially for elderly users).

According to a variation, the at least one tensioning element provides a closing effect on the handle or urges the handle toward the on position. This beneficially reduces the physical effort required to put the handle into the on position. Additionally, and in contrast to prior art tightening systems such as dial tensioners and electrical switches, the closing effect on the handle safely stows the tensioning unit in the on position, reducing the risk of accidental release, thereby improving user safety.

According to a variation, the tightening system includes one or more elastic elements operatively coupled to the handle and the at least one tensioning element to permit automatic volume adaption of the adjustable socket system. "Automatic" means "without human intervention." For instance, when the handle is moved from the off position to the on position, the elastic elements can be configured to deflect so that the volume of the adjustable socket system can adapt or adjust to more closely match that of a residual limb. This advantageously improves comfort and ease of use, especially for users with limited dexterity or cognition.

BRIEF DESCRIPTION OF THE DRAWINGS

These and other features, aspects, and advantages of the present disclosure will become better understood regarding the following description, appended claims, and accompanying drawings.

FIG. 4A is a partial schematic view of the tensioning unit in the socket system of FIG. 1 in the open configuration according to an embodiment.

FIG. 4B is a partial schematic view of the tensioning unit in the socket system of FIG. 1 in the closed configuration according to an embodiment.

FIG. 5 is a side view of the displacement wheel in the socket system of FIG. 1 according to an embodiment.

FIG. 6 is a partial schematic view of the tightening system in the socket system of FIG. 1 according to an embodiment.

FIG. 7 is a side view of a tensioning unit according to another embodiment.

FIG. 8 is a partial schematic view of a tightening system including the tensioning unit in FIG. 7.

FIG. 9 is an exploded view of a secondary tensioner according to an embodiment.

FIG. 11A is a schematic view of the tensioning unit in the socket system of FIG. 10A in an off position.

FIG. 11B is a schematic view of the tensioning unit in the socket system of FIG. 10A in an on position.

FIG. 12 is a partially exploded view of a secondary tensioner according to another embodiment.

FIG. 13 is a schematic view of a volume adjustment system according to an embodiment.

FIG. 14 is a perspective view of a grip portion according to another embodiment

FIG. 15A is a schematic view of a tensioning unit in a first position according to another embodiment.

FIG. 15B is a schematic view of the tensioning unit in FIG. 15A in a second position.

FIG. 16 is a partial side view of a tensioning unit according to another embodiment.

FIG. 17 is a side view of an adjustable socket system according to another embodiment.

DETAILED DESCRIPTION OF VARIOUS EMBODIMENTS

Figure 1:
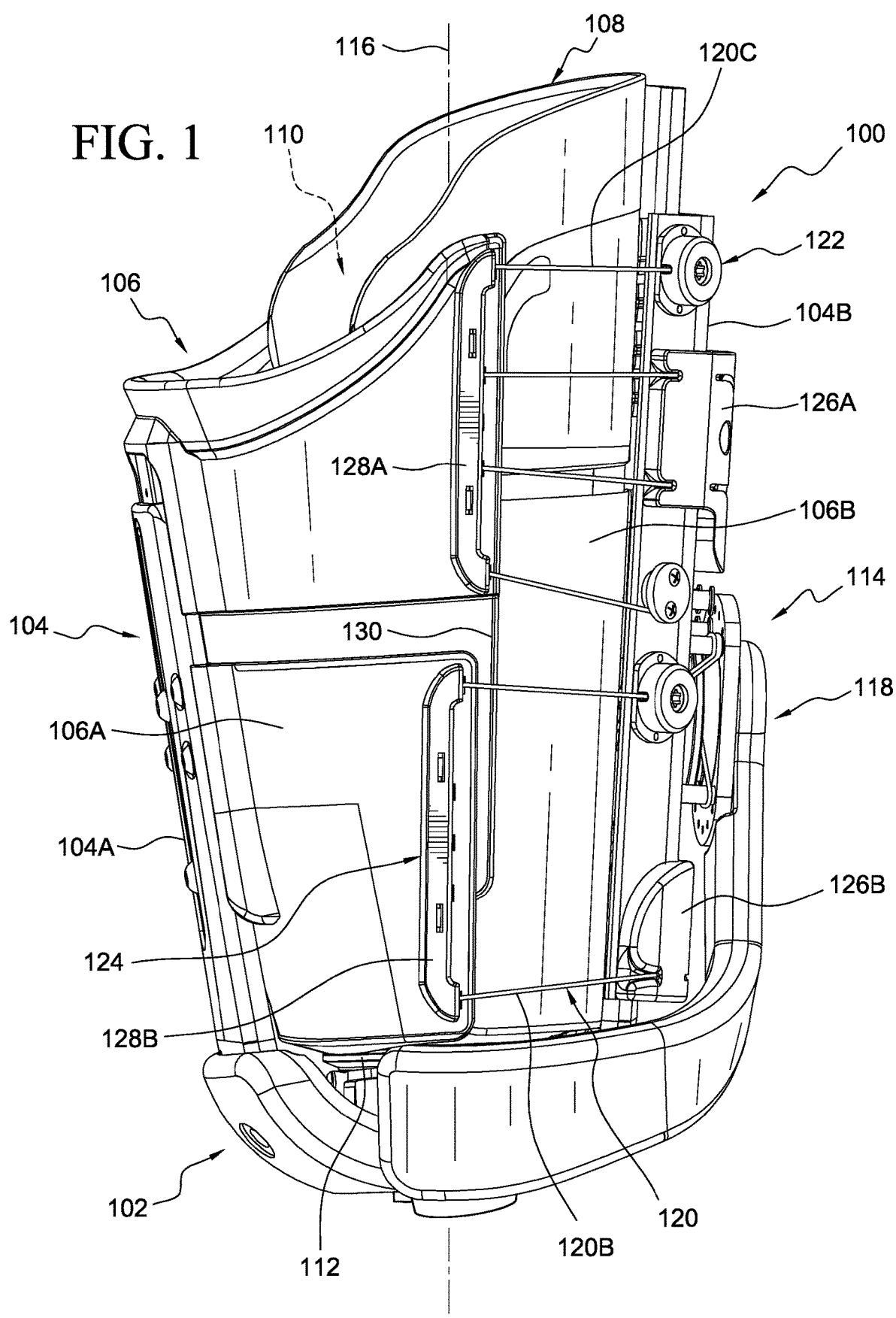
FIG. 1 is a side view of a socket system according to an embodiment.
Figure 2:
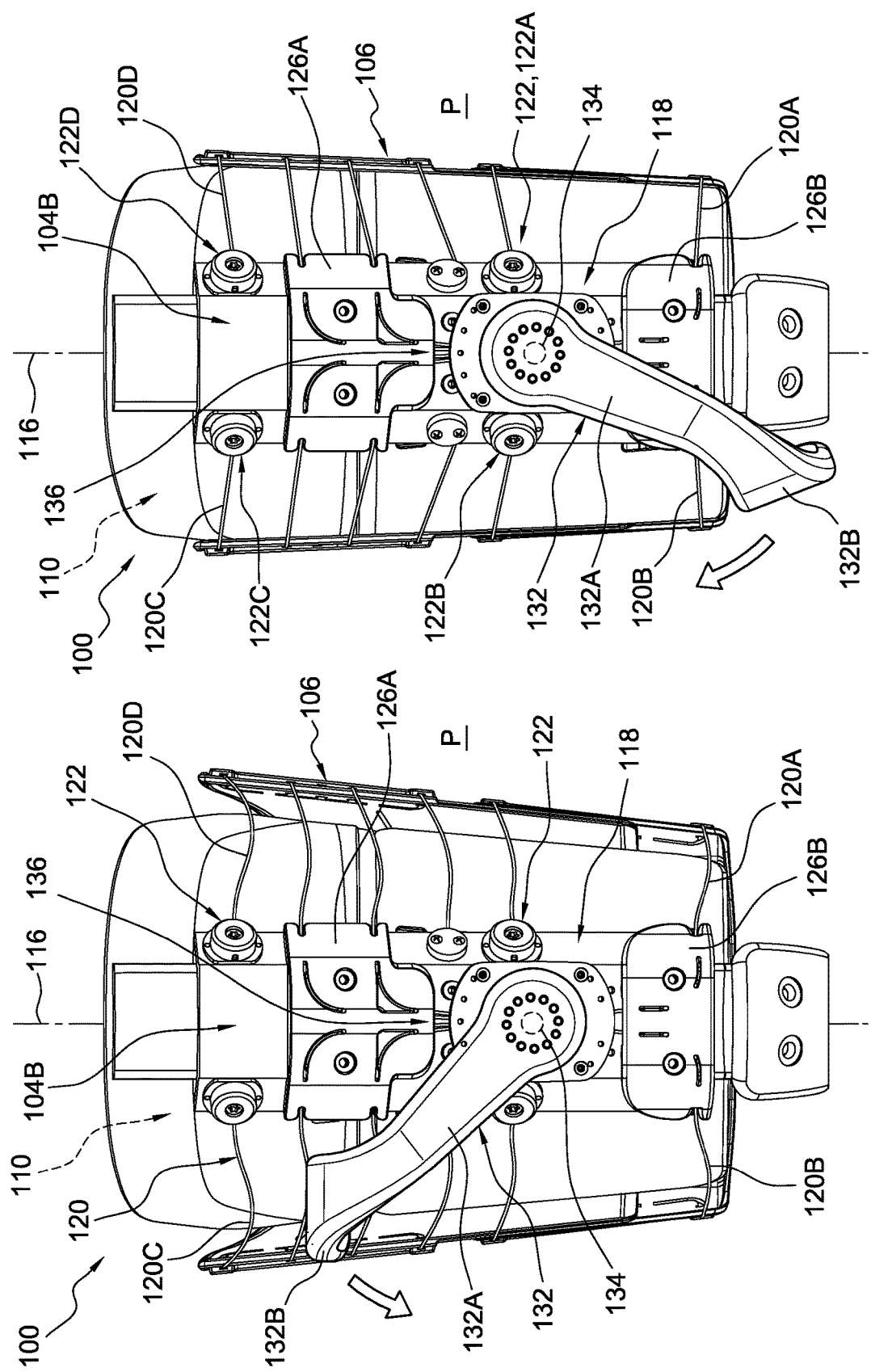
FIG. 2A is a front view of the socket system in FIG. 1 in an open configuration according to an embodiment.
FIG. 2B is a front view of the socket system in FIG. 1 in a closed configuration according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112(f).

FIGS. 1-6 illustrate an adjustable socket system 100 according to an embodiment. As seen in FIG. 1, the socket system 100 can include a base 102, a plurality of longitudinal supports 104 connected to the base 102, and a plurality of shell components 106 connected to the supports 104. The shell components 106 collectively form a socket wall 108 defining a receiving volume 110 adapted to receive a residual limb. The shell components 106 can include a medial shell component 106A that wraps around and engages at least a medial aspect of the residual limb, and a lateral shell component 106B that wraps around and engages at least a lateral aspect of the residual limb. The shell components 106 can be formed of plastic materials, such as thermoplastic or thermosetting polymers, fiber reinforced plastic, polypropylene, polyethylene, molded chopped fibers, or any other suitable materials.

The base 102 is arranged to provide support for a distal end of the residual limb and can include at least one coupling device 112 for fixing or securing the residual limb or a liner to the base 102. The base 102 and longitudinal supports 104 can be formed of any suitable material. For example, the base 102 and/or the longitudinal supports 104 can be formed of metal or molded parts including plastic with carbon fiber mixed therein.

The socket system 100 is radially adjustable between an open configuration and a closed configuration. A tightening system 114 is arranged to move the socket system 100 between the open and closed configurations. In the open configuration (shown in FIG. 2A), at least some of the longitudinal supports 104 and/or shell components 106 are free to move or are forced radially outward relative to a longitudinal axis 116 of the socket system 100, increasing the receiving volume 110 or increasing a circumference of the socket system 100. This effectively loosens the fit of the socket system 100 on a residual limb inserted in the receiving volume 110 or decreases the loading on the residual limb from the socket wall 108.

In the closed configuration (shown in FIG. 2B), at least some of the longitudinal supports 104 and/or the shell components 106 are moved or forced radially inward relative to the open configuration, decreasing the receiving volume 110 or decreasing the circumference of the socket system 100. For instance, the longitudinal supports 104 can include a medial support 104A having an elongate configuration and a lateral support 104B having an elongate configuration. At least one of the medial or lateral supports 104A, 104B can be pivotally connected to the base 102 such that in the closed configuration at least one of the medial or lateral supports 104A, 104B is rotated or folded toward the other to decrease the receiving volume 110. This tightens or secures the fit of the socket system 100 on a residual limb inserted in the receiving volume 110 and/or increases the loading on the residual limb from the socket wall 108. It will be appreciated that movement of any suitable portion of a support or shell component can move the socket system 100 between the open and closed configurations.

The tightening system 114 includes a tensioning unit 118, one or more tensioning elements 120 operatively coupled to the tensioning unit 118, and one or more secondary tensioners 122 operatively coupled to the one or more tensioning elements 120. It will be appreciated that the tensioning elements 120 may be formed of line, cord, wire, string, combinations thereof, or any other suitable element.

The tensioning elements 120 are routed through a plurality of guides 124 on the shell components 106 and/or longitudinal supports 104, facilitating tightening of the socket system 100. For instance, the tensioning elements 120 can extend from the tensioning unit 118 through upper and lower guides 126A, 126B on the lateral support 104B, which, in turn direct the tensioning elements 120 through upper and lower guides 128A, 128B located along or near leading edges 130 of the medial shell component 106A.

In an embodiment, the tensioning elements 120 can include a first tensioning element 120A (shown in FIG. 2A) forming a first loop over a distal posterior region of the lateral aspect of the socket system 100, a second tensioning element 120B forming a second loop over a distal anterior region of the lateral aspect, a third tensioning element 120C forming a third loop over a proximal anterior region of the lateral aspect, and a fourth tensioning element 120D (all shown in FIG. 2A) forming a fourth loop over a proximal posterior region of the lateral aspect of the socket system 100. Increasing tension in the tensioning elements 120A, 120B, 120C, 120D reduces the circumference of the loops, which, in turn pulls the leading edges 130 of the medial shell component 106A together, tightening the fit of the socket system 100 on the residual limb. While the tensioning elements 120 are described forming loops, it will be appreciated that the tensioning elements 120 can be routed on the socket system 100 in any suitable configuration and on any suitable region of the socket system 100. For instance, the tensioning elements 120 can be routed in a zig-zagging pattern between the lateral guides 126A, 126B and the medial guides 128A, 128B.

This grouping of guides 124 allows the tightening system 114 to tighten and/or loosen the socket system 100 by actively tensioning a limited region rather than wrapping and/or tightening cables or wires about the entire or substantial entirety of the socket wall 108, improving user comfort. This helps reduce the overall profile of the socket system 100. It also helps limit pressure points from forming on different areas of the residual limb. Pressure points on the residual limb can be problematic in that the pressure points cause irritation, pain, and discomfort to the user. Further, when the tensioning elements 120 are tensioned, they tend to tension or pull the medial shell component 106A tight around the residual limb rather than compress directly on the residual limb, further increasing user comfort.

The upper and lower guides 126A, 126B can be integrated into the lateral support 104B, lowering the overall profile of the socket system 100 and improving structural reliability. The upper and lower guides 126A, 126B can alternatively be attached to the lateral support 104B. The upper and lower guides 126A, 126B can define elongated linear and/or curved pathways that direct the tensioning elements 120 between the tensioning unit 118 and upper and lower guides 128A, 128B on the medial shell component 106A, reducing friction in the tightening system 114.

Referring now to FIGS. 2A and 2B, the socket system 100 can be easily opened or closed with a simple manipulation of the tensioning unit 118 between off and on positions, respectively. In an embodiment, the tensioning unit 118 comprises a handle 132 defining a moment arm rotatable about a rotation axis 134 and operatively coupled to the tensioning elements 120.

In the off position (shown in FIG. 2A), slack or low tensions levels in the tensioning elements 120 can allow the socket system 100 to move toward the open configuration. In the on position (shown in FIG. 2B), the handle 132 effectively pulls and/or shortens the length of the tensioning elements 120 forming the loops, which, in turn, tensions the tensioning elements 120 and the shell components 106 to move the socket system 100 to the closed configuration. More particularly, the tensioning elements 120 are connected to the tensioning unit 118 via at least one movable connection point 138 (shown in FIG. 4A) that shifts toward and away from at least one control point 136 (also shown in FIG. 4A) that directs the tensioning elements 120 between the tensioning unit 118 and the shell component 106 and/or longitudinal supports 104. This shifting of the movable connection point 138 relative to the control point 136 displaces the tensioning elements 120 extending from the tensioning unit 118 up or down along the longitudinal axis 116. In an embodiment, the movable connection point 138 can be operatively associated with the handle 132 and the control point 136 can be defined by at least one of the guides 126A, 126B. In other embodiments, the control point 136 can be defined by at least one of the guides 128A, 128B or any other suitable point along the tensioning elements 120 between the shell components 106 and the tensioning unit 118.

Movement of the handle 132 from the off position to the on position shifts the movable connection point 138 away from the control point 136, which, in turn, displaces the tensioning elements 120 up or down along the longitudinal axis 116. This tensions the tensioning elements 120 and the shell components 106 to move the socket system 100 to the closed configuration. Because the handle 132 defines a moment arm it provides the user a mechanical advantage, as it requires less user strength to move the tensioning unit 118 between the on position and off position.

In addition, the tensioning unit 118 can have a binary configuration such that a user can only position and/or lock the handle 132 in the on position or the off position. In other words, the tensioning unit 118 is either on or off, providing an intuitive and simple manner for users with limited dexterity or cognition to don and doff the socket system 100. This is beneficial over known tightening systems such as dial tensioners or strap systems which require complex levels of manual dexterity, making their use difficult and intimidating for many users. The binary configuration of the tensioning unit 118 also controls the basic fit of the socket system 100 on the residual limb rather than requiring the user to precisely fit the system with straps or dial tensioners, as in the prior art. This substantially decreases the likelihood that a user will over-tighten or under-tighten the socket system 100, and improves ease of use and safety, especially for elderly users. According to a variation, the binary configuration of tensioning unit 118 permits the user to only lock the handle 132 in the on position.

In an embodiment, the tensioning elements 120 provide a closing effect on the handle 132 or urge the handle 132 toward the on position. For example, the tensioning elements 120 can be located and configured to pull the handle 132 toward the on position or in the posterior direction P when the handle 132 reaches a critical angle about the rotation axis 134, providing the closing effect on the handle 132.

It will be appreciated that the tightening system 114 may provide a closing effect on the handle 132 via other means. For instance, the tensioning unit 118 and/or base 102 can include magnets, ferromagnetic material, and/or ferrous material to form a magnetic attraction between the handle 132 and the base 102, achieving a closing effect on the handle 132 toward the on position. In other embodiments, the tensioning unit 118 can include a latch release mechanism that selectively stows the handle 132 in the on position, achieving a closing effect.

In the illustrated embodiment, the handle 132 includes a connecting portion 132A and a grip portion 132B connected to the connecting portion 132A and curving toward the medial support 104A (shown in FIG. 1). The grip portion 132B can be wider than the connecting portion 132A and its orientation and arrangement provides a large and ergonomic gripping area for the user, making operation of the handle 132 easier for users with limited dexterity. Moreover, the elongate configuration of the connecting portion 132A provides a user with greater mechanical advantage, requiring less user strength to move the tensioning unit 118 between the on position and off position. The handle 132 can be formed of any suitable material such as metal, plastic, carbon fiber, combinations thereof, or any other material which would provide sufficient strength to resist unwanted deformation during use or accidental contact with external objects.

As best seen in FIG. 2B, when the handle 132 is in the on position, the connecting portion 132A extends downwardly and the grip portion 132B wraps around an anterior side of the base 102. This beneficially locates the grip portion 132B substantially adjacent the base 102 and below the shell components 106, lowering the general profile of the handle 132 on the socket system 100 and reducing the risk of it being dislodged by accidental contact with external objects. The positioning of the handle 132 on the anterior side of the base 102 also allows the base 102 and/or the lateral support 104B to partially shield the handle 132 in the on position, further reducing the risk of the handle 132 being dislodged by accidental contact.

The tensioning unit 118 thus provides a binary system that beneficially facilitates donning and doffing of the socket system 100 as good hand dexterity and/or strength is not required to operate the tensioning unit 118. The tensioning unit 118 also decreases and/or eliminates the likelihood that a user will over-tighten and/or under-tighten the socket system 100 on the residual limb, enhancing safety and comfort. It will be appreciated that while the tightening system 114 is generally described on the lateral aspect of the socket system 100, this and other tightening systems of the present disclosure can be adapted for use on the medial, anterior, or posterior aspect of the socket system 100 to achieve the same or similar benefits.

The secondary tensioners 122 enable tension control of the tensioning elements 120 independent of the tensioning unit 118. This allows for adjustment or control of tension in a tensioning elements 120 even when the tensioning elements 120 are under a load. For instance, when the tensioning unit 118 is in the on position, a clinician or certified prosthetist orthotist ("CPO") can manipulate at least one of the secondary tensioners 122 to fine tune the fit or loading of the socket system 100 on the residual limb.

If the fit of the socket system 100 is too loose, at least one of the secondary tensioners 122 can be manipulated to decrease the length of at least one of the tensioning elements 120 and thereby increase tension in the tensioning element 120. If the fit of the socket system 100 is too tight, at least one of the secondary tensioners 122 can be manipulated to increase the length of at least one of the tensioning elements 120 and thereby decrease tension in the tensioning elements 120.

The secondary tensioners 122 can be connected to different tensioning elements 120. For example, the secondary tensioners can include a first secondary tensioner 122A connected to the first tensioning element 120A, a second secondary tensioner 122B connected to the second tensioning element 120B, a third secondary tensioner 122C connected to the third tensioning element 120C, and a fourth secondary tensioner 122D connected to the fourth tensioning element 120D.

The first and second secondary tensioners 122A, 122B can be located on opposite sides of the lateral support 104B and the third and fourth secondary tensioners 122C, 122D can be located above the first and second secondary tensioners 122A, 122B on opposite sides of the lateral support 104B. This allows the loading or fit of the socket system 100 to be proportionally or differentially adjusted using different ones of the secondary tensioners 122A, 122B, 122C, 122D.

The secondary tensioners 122 can comprise spool units, worm gear units, torque units, friction plates, turn dial units, or any other suitable mechanisms. Four secondary tensioners 122A, 122B, 122C, 122D are shown but the tightening system 114 can include any suitable number of secondary tensioners 122.

Figure 3:
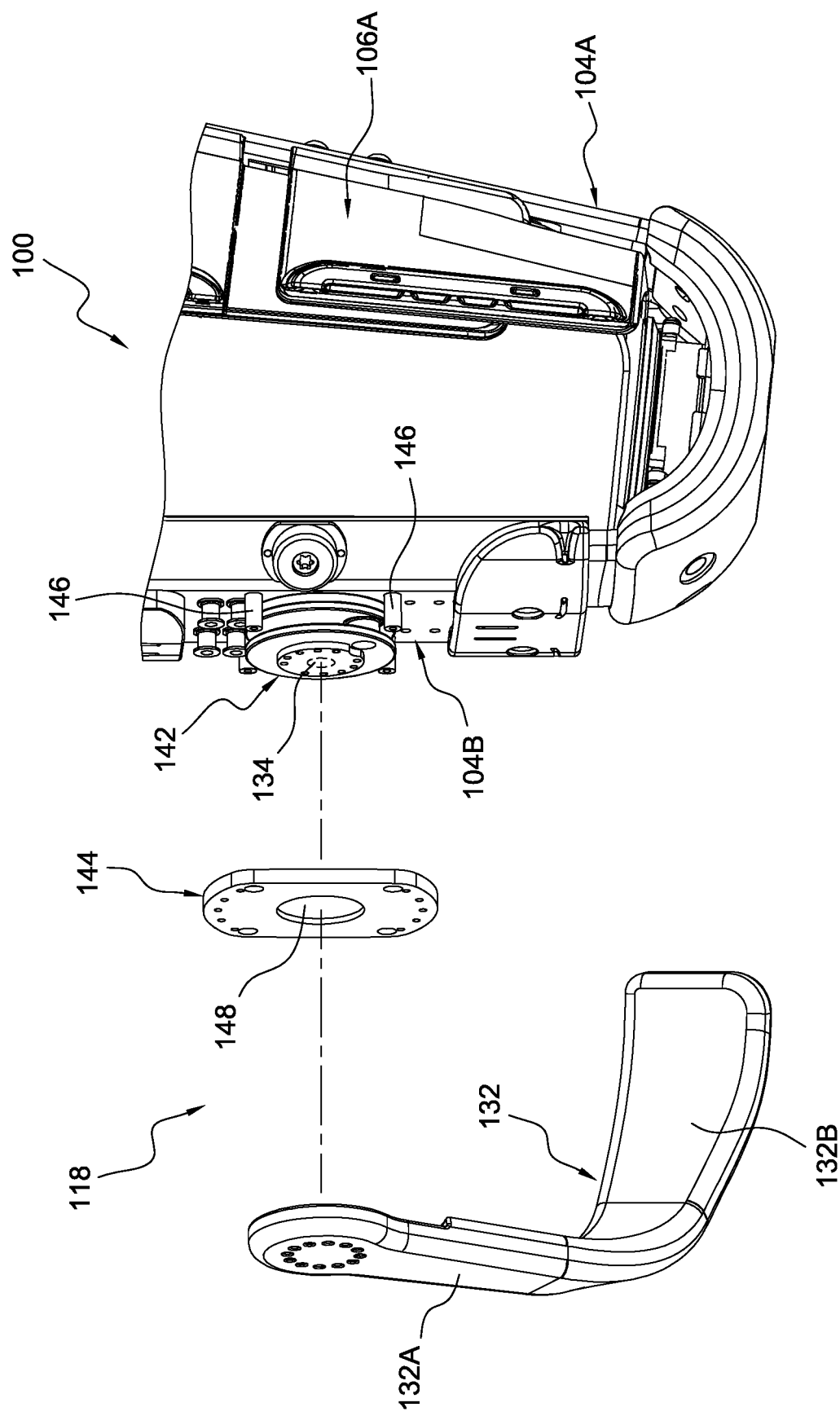
FIG. 3 is a partial exploded view of the tensioning unit in the socket system of FIG. 1.

FIG. 3 shows a partial exploded view of the tensioning unit 118 according to an embodiment. The tensioning unit 118 includes the handle 132, a displacement member comprising a displacement wheel 142 rotatably mounted on the lateral support 104B, and a protective plate 144 secured over the displacement wheel 142 via a plurality of support posts 146. The handle 132 is attached to the displacement wheel 142 via an opening 148 formed in the protective plate 144. Movement of the handle 132 between the on position and the off position rotates the displacement wheel 142 about the rotation axis 134.

Referring to FIGS. 4A and 4B, the displacement wheel 142 includes the movable connection point 138 comprising a pulley assembly 150 engaging one or more of the tensioning elements 120. The pulley assembly 150 includes a pin 152 and a pulley 154 mounted on the pin 152. The pulley 154 may be fixedly attached to the pin 152 or the pulley 154 may rotate on the pin 152. The pulley assembly 150 moves in a circular path on the displacement wheel 142 when the displacement wheel 142 rotates about the rotation axis 134. A variable distance D is defined between the movable connection point 138 and the control point 136. Optionally, the displacement wheel 142 includes a plurality of attachment holes for varying the position of the pulley assembly 150 on the displacement wheel 142.

As seen, a first end of the tensioning element 120A can be attached to a first anchor point 156. The first anchor point 156 may comprise one of the support posts 146. From the first anchor 156 point, the first tensioning element 120A extends to the movable connection point 138 or pulley assembly 150 where the first tensioning element 120A partially loops around the pulley assembly 150, which directs it toward the control point 136. To enhance displacement of the tensioning element 120, the tensioning element 120 can be looped around the pulley assembly 150 one or more times. In the illustrated embodiment, the first and second tensioning elements 120A, 120B are engaging the pulley assembly 150.

FIG. 4A shows the tensioning unit 118 in the off position with the two tensioning elements 120A, 120B passing over the pulley assembly 150, one to the first anchor point 156 and the other to a second anchor point 158. When the tensioning unit 118 moves to the on position, the pulley assembly 150 or movable connection point 138 moves along a circular path on the displacement wheel 142, moving the pulley assembly 150 or movable connection point 138 upward relative to the control point 136 as seen in FIG. 4B.

This increases the distance D between the movable connection point 138 and the control point 136 and displaces the tensioning elements 120A, 120B in an upward direction, which, in turn, tensions the tensioning elements 120A, 120B and the shell components 106 to move the socket system 100 to the closed configuration.

When the pulley assembly 150 reaches a critical angle Y, the tensioning elements 120A, 120B can pull the handle 132 toward the base 102 or in a posterior direction P. This provides a closing effect that safely stows the handle 132 and decreases the risk of accidental release. In an embodiment, the critical angle Y can be greater than about 180 degrees, about 181 degrees, about 182 degrees, about 185 degrees, or about 190 degrees relative to the location of the pulley assembly 150 when the tensioning unit 118 is in the off position.

FIG. 5 illustrates a displacement wheel 142 according to an embodiment. The displacement wheel 142 defines a mounting area 160 for attachment of the handle 132 and includes a first movable connection point 138A comprising a first pulley assembly 150A extending between a first plate 162 and a second plate 164, and a second movable connection point 138B comprising a second pulley assembly 150B extending between the second plate 164 and a third plate 166.

The first and second pulley assemblies 150A, 150B can be radially offset relative to the longitudinal axis 116. For instance, they can be at different levels on the displacement wheel 142 such that rotation of the displacement wheel 142 moves the first pulley assembly 150A in an arcuate path with the second pulley assembly 150B moving in an arcuate path above the first pulley assembly 150A. Having first and second pulley assemblies 150A, 150B at different levels on the displacement wheel 142 permits at least some of the tensioning elements 120 to be separated from one another during use of the tensioning unit 118. For instance, the first and second tensioning elements 120A, 120B can be connected to the first pulley assembly 150A, and the third and fourth tensioning element 120C, 120D can be connected to the second pulley assembly 150B. This reduces friction on the tensioning elements 120, which, in turn, decreases the physical effort needed to move the handle 132 to the on position. The reduction in friction also decreases wear and tear on the tensioning elements 120 and components in contact with the tensioning elements 120.

The first and second pulley assemblies 150A, 150B can be angularly offset relative to one another. For instance, the first and second pulley assemblies 150A, 150B can be offset about 180 degrees or by some other angular distance. This helps ensure that when the handle 132 is moved to the on position both the lower tensioning elements 120A, 120B and the upper tensioning elements 120C, 120D are tensioned.

The angular offset between the first and second pulley assemblies 150A, 150B can also form a constant force mechanism so that the input force required to move the handle 132 between the on and off positions is substantially constant over the range of motion of the handle 132. For example, as the tensioning unit 118 moves between the on and off positions, the forces on the first and second pulley assemblies 150A, 150B from the tensioning elements 120A, 120B, 120C, 120D can generally oppose one another so that an input force required to move the handle 132 is substantially constant over the range of motion of the handle 132. This can help facilitate operation of the tightening system 114 for users with limited strength and/or dexterity.

FIG. 6 is a schematic view of the tightening system 114 according to an embodiment. A first end of the first tensioning element 120A is attached to the first anchor point 156 on or near a support base 168 for the tensioning unit 118. The support base 168 can be attached to or integrated into the lateral longitudinal support 104B and/or the lateral shell component 106B. The first anchor point 156 may comprise any suitable structure such as one of the support posts 146 (shown in FIG. 3). From the first anchor point 156, the first tensioning element 120A extends to the first movable connection point 138A comprising the first pulley assembly 150A. The first pulley assembly 150A then directs the first tensioning element 120A to a first control point 136A. The first control point 136A can comprise the lower guide 126B. The lower guide 126B then directs the first tensioning element 120A to the lower guide 128B on the posterior side P of the medial shell component 106A. The lower guide 128B then directs the first tensioning element 120A to the first secondary tensioner 122A. A second end of the first tensioning element 120A is attached to the first secondary tensioner 122A.

A first end of the second tensioning element 120B is attached to the second anchor point 158 on or near the support base 168. From the second anchor point 158, the second tensioning element 120B extends to the first movable connection point 138A or first pulley assembly 150A. The first pulley assembly 150A then directs the second tensioning element 120B toward the first control point 136A or the lower guide 126B. The lower guide 126B then directs the second tensioning element 120B to a lower guide 128B on the anterior side A of the medial shell component 106A. The lower guide 128B then directs the second tensioning element 120B to the second secondary tensioner 122B. A second end of the second tensioning element 120B is attached to the second secondary tensioner 122B.

A first end of the third tensioning element 120C is attached to a third anchor point 170 on or near the support base 168. From the third anchor point 170, the third tensioning element 120C extends through the upper guide 128A on the anterior side A of the medial shell component 106A. The upper guide 128A then directs the third tensioning element 120C to a second control point 136B comprising the upper guide 126A on the lateral support 104B. The third tensioning element 120C then extends to a second movable connection point 138B comprising the second pulley assembly 150B. From the second movable connection point 138B, the third tensioning element 120C loops around the support post 146 on the anterior side A, back around the second pulley assembly 150B, and then back to the second control point 136B and through the upper guide 126A. From the upper guide 126A, the third tensioning element 120C extends again through the upper guide 128A, which, in turn, directs the third tensioning element 120C to the third secondary tensioner 122C. A second end of the third tensioning element 120C is attached to the third secondary tensioner 122C.

A first end of the fourth tensioning element 120D is attached to a fourth anchor point 172 on or near the support base 168. From the fourth anchor 172 point, the fourth tensioning element 120D extends through the upper guide 128A on the posterior side P of the medial shell component 106A. The upper guide 128A then directs the fourth tensioning element 120D to the second control point 136B or the upper guide 126A on the lateral support 104B. The fourth tensioning element 120D then extends to the second movable connection point 138B or the second pulley assembly 150B. From the second movable connection point 138B, the fourth tensioning element 120D loops around the support post 146 on the anterior side A, extends again around the second pulley assembly 150B, and then back to the second control point 136B and through the upper guide 126A. From the upper guide 126A, the fourth tensioning element 120D extends again through the upper guide 128B, which, in turn, directs the fourth tensioning element 120D to the fourth secondary tensioner 122D. A second end of the fourth tensioning element 120D is attached to the fourth secondary tensioner 122D.

When the handle 132 is moved to the on position, the displacement wheel 142 rotates in a first direction about the rotation axis 134, which, in turn, moves the first movable connection point 138A (e.g., the first pulley assembly) upwardly away from the first control point 136A (e.g, the lower guide 126B). This displaces the first and second tensioning elements 120A, 120B in an upwardly direction, which in turn tensions the first and second tensioning elements 120A, 120B and tightens a distal region of the socket system 100.

Rotation of the displacement wheel 142 in the first direction simultaneously moves the second movable connection point 138B (e.g., the second pulley assembly) downwardly away from the second control point 136B (e.g., the upper guide 126A). This displaces the third and fourth tensioning elements 120C, 120D in a downwardly direction, which, in turn, tensions the third and fourth tensioning elements 120C, 120D and tightens a proximal region of the socket system 100. As seen, the first and second pulley assemblies 150A, 150B can be angularly offset about 180 degrees to help ensure that when the handle 132 turns, all of the tensioning elements 120 tension. Further, the first and second pulley assemblies 150A, 150B can be located at different levels on the displacement wheel 142 to reduce friction on the tensioning elements 120.

When the handle 132 is moved to the off position, the displacement wheel 142 rotates in a second direction opposite the first, allowing the tensioning elements 120A, 120B, 120C, 120D and the movable connection points 138A, 138B to return toward their original positions, reducing tension in the tensioning elements and permitting the socket system 100 to move to the open configuration. It will be appreciated that the number and routing of the tensioning elements 120 on the tightening system 114 is exemplary only as different numbers of tensioning elements and different paths are possible.

Optionally, the tightening system 114 can include one or more elastic elements to permit automatic volume adaptation of the socket system 100. More particularly, when the handle 132 is moved from the off position to the on position, the elastic elements can be arranged to deflect so that a volume of the adjustable socket system can adapt or adjust to more closely match that of the residual limb. This beneficially improves comfort and ease of use of the socket system 100, especially for users with limited dexterity or cognition.

FIGS. 7 and 8 illustrate a tightening system 214 according to another embodiment. The tightening system 214 is similar or generally the same as the tightening system 114 except that it includes a plurality of elastic elements that permit automatic volume adaption of the socket system 100. For instance, the tightening system 214 includes a tensioning unit 218, one or more tensioning elements 220 arranged to interact with the tensioning unit 218, and one or more secondary tensioners 222 operatively coupled to the tensioning elements 220. The tensioning elements 220 are routed through a plurality of guides 124 on the medial shell component 106A. As seen, the tensioning elements 220 include four tensioning elements 220A, 220B, 220C, and 220D. Each tensioning element 220A, 220B, 220C, and 220D includes an end attached to a corresponding secondary tensioner 222A, 222B, 222C, 222D and interacts with one of the first and second pulley assemblies 250A, 250B carried on the displacement wheel 242.

The tensioning unit 218 includes a handle 232 operatively coupled to the tensioning elements 220. The handle 232 defines a moment arm attached to a displacement wheel 242 that is rotatable about a rotation axis 234. The displacement wheel 242 carries a first movable connection point 238A comprising the first pulley assembly 250A and a second movable connection point 238B comprising the second pulley assembly 250B that engage or interact with the tensioning elements 220 and move along a circular path about the rotation axis 234. The first and second tensioning elements 220A, 220B include one or more segments extending between the first pulley assembly 250A and a first control point 236A comprising the lower guide 228B. The third and fourth tensioning elements 220C, 220D includes one or more segments extending between the second pulley assembly 250B and a second control point 236B comprising the upper guide 228A.

In the off position, tension levels or slack in the tensioning elements 220 can permit the adjustable socket system 100 to move toward the open configuration. The engagement or interaction between the tensioning elements 220 and the pulley assemblies 250A, 250B is such that movement of the handle 232 from the off position to the on position displaces the pulley assemblies 250A, 250B up or down relative to the first and second control points 236A, 236B, which, in turn, displaces the tensioning elements 220 up or down along the longitudinal axis 216. This displacement tensions the tensioning elements 220 and the shell components 106 to move the socket system 100 to the closed configuration. The tensioning unit 218 can have a binary configuration such that a user can only lock the handle 232 in the on position or the off position, providing an intuitive and simple manner for users with limited dexterity or cognition to don and doff the socket system 100. The binary configuration of the tensioning unit 118 also decreases and/or eliminates the likelihood that a user will over-tighten and/or under-tighten the socket system 100 on the residual limb, enhancing safety and comfort. According to a variation, the binary configuration of tensioning unit 218 permits the user to only lock the handle 232 in the on position.

The elastic elements 274 are operatively coupled to the handle 232 and the tensioning elements 220 to permit automatic volume adjustment of the socket system 100. For instance, each tensioning element 220A, 220B, 220C, 220D is operatively connected to the handle 232 and a corresponding elastic element 274A, 274B, 274C, 274D positioned in a housing unit 276 mountable on the lateral support 104B. The housing unit 276 can protect the elastic elements 274 and reduce the likelihood of injury from the elastic elements. The housing unit 276 can define windows 277 corresponding to the elastic elements 274 which allow a user or clinician to observe loading of the elastic elements 274. The elastic elements 274A, 274B, 274C, 274D are shown as compression springs but can be constant force springs, pre-tension springs, variable tension springs, combinations thereof, or any other suitable elastic element.

Movement of the handle 232 from the off position to the on position displaces the tensioning elements 220A, 220B, 220C, 220D up or down, which, in turn, loads the elastic elements 274A, 274B, 274C, 274D in the housing unit 276. As the load is applied, the elastic elements deflect or get shorter. As the load is reduced or removed, the stored energy in the elastic elements moves them back toward their equilibrium length. The deflection of the elastic elements 274A, 274B, 274C, 274D allows the fit of the socket system 100 to adapt to the shape of the residual limb.

For instance, if a proximal region of the residual limb has a larger circumference, the residual limb can hold back the shell components 106 in the proximal region as the tensioning unit 218 moves the socket system 100 toward the closed configuration, which, in turn, causes the third and fourth tensioning elements 220C, 220D to load and/or shorten the elastic elements 274C, 274D. Within an elastic range of the elastic elements 274C, 274D, the amount of deflection or shortening of the elastic elements 274C, 274D increases with the magnitude of the load on the elastic elements 274C, 274D. This shortening of the elastic elements 274C, 274D effectively increases a length of the tensioned third and fourth tensioning elements 220C, 220D outside of the tensioning unit 218, allowing an increased circumference of the proximal region of the shell components 106 when the socket system 100 enters the closed configuration.

As such, deflection of the elastic elements 274 automatically adjusts the volume of the socket system 100 to better match the dimensions of the residual limb. Moreover, it will be appreciated that because the elastic elements 274A, 274B, 274C, 274D are generally independent of one another, the fit of the socket system 100 on different regions of the residual limb can be different. In other embodiments, the tensioning elements 220 can be connected to a common elastic element. Four tensioning elements and elastic elements are shown, but any number is possible.

Optionally, the tightening system 214 can include a lockout system that fixes the length of the elastic elements 274A, 274B, 274C, 274D once the tensioning unit 218 is in the on position. This helps makes it so that the elastic elements 274A, 274B, 274C, 274D cannot deflect to increase or decrease the volume of the socket system 100 when the socket system 100 is in the closed configuration or bearing weight, thus enhancing stability.

FIG. 9 illustrates a secondary tensioner 322 according to an embodiment. The secondary tensioner 332 includes a housing 376, a spool 378, and a lid 380. The spool 378 is situated within the housing 376 such that the spool 378 is rotatable relative to the housing 376. The housing 376 can be attached to a support base 168 (shown in FIG. 6) or integrated with other components of the socket system 100. A tensioning element 220 can be attached to the spool 378 via an opening 382 formed in the housing 376.

When the spool 378 rotates in a tightening direction, the tensioning element 220 is drawn into the housing 376 and is wound around the spool 378. As the tensioning element 220 is wound around the spool 378, tension in the tensioning element 220 increases, causing the socket system 100 to tighten. When the spool 378 rotates in a loosening direction, the tensioning element 200 unwinds from the spool 378 and at least part of the tensioning element 220 exits the housing 376. As the tensioning element 220 unwinds from the spool 378, tension in the tensioning element 220 decreases, loosening the socket system 100.

A spring member 384 can be disposed between the housing 376 and the spool 378 that forces the upper surface of the spool 378 into engagement with a lower surface of the lid 380. The spool 378 and lid 380 define corresponding engagement features arranged to only allow the spool 378 to rotate relative to the housing 376 via an external input. For instance, the lid 380 includes an upper opening 386 and the spool 378 defines a socket 388, each arranged to receive a tool member (e.g., a wrench or key) so that a CPO or user can rotate the spool 378 to adjust tension in the tensioning element 220. The secondary tensioner 322 thus beneficially permits adjustment or control of tension in a tensioning element 220 even when the tensioning element is under a load.

In an embodiment, the secondary tensioner 322 can be arranged for use with a torque wrench that provides an indicator (e.g., a click) when a desired torque in the secondary tensioner 322 has been attained. This helps determine when an appropriate tension is applied to the residual limb during fitting of the socket system 100. In other embodiments, the secondary tensioner 322 can comprise a worm gear unit or any other suitable mechanism.

FIGS. 10A-13 illustrate yet another embodiment of an adjustable socket system 400 including an alternative tightening system. The socket system 400 includes a base 402 arranged to provide support for a distal end of a residual limb, a plurality of longitudinal supports 404 connected to the base 402, and a plurality of shell components 406 connected to the supports 404. The shell components 406 collectively form a socket wall 408 defining a receiving volume adapted to receive the residual limb. A tightening system 414 is arranged to move the socket system 400 between open and closed configurations.

In the open configuration (shown in FIG. 10A), at least some of the longitudinal supports 404 and/or shell components 406 are free to move or be forced radially outward relative to a longitudinal axis 416 of the socket system 400, increasing the receiving volume or increasing a circumference of the socket system 400. This effectively loosens the fit of the socket system 400 on a residual limb inserted in the receiving volume or decreases the loading of the residual limb from the socket wall 408. In the closed configuration (shown in FIG. 10B), at least some of the longitudinal supports 404 and/or the shell components 406 are moved or forced radially inward relative to the open configuration, decreasing the receiving volume or decreasing the circumference of the socket system 400. This tightens or secures the fit of the socket system 400 on the residual limb and/or increases the loading on the residual limb from the socket wall 408.

The tightening system 414 includes the tensioning unit 418, one or more tensioning elements 420 operatively coupled to the tensioning unit 418, and one or more secondary tensioners 422 operatively coupled to the tensioning elements 420. The tensioning elements 420 may be formed of line, cord, wire, string, combinations thereof, or any other suitable element.

The tensioning elements 420 can be routed through a plurality of guides 424 on the shell components and/or the supports. For instance, the tensioning elements 420 can extend from the tensioning unit 418 through a guide 426 on a lateral support 404B, which, in turn, directs the tensioning elements 420 through upper and lower guides 428A, 428B located along or near leading edges 430 of a medial shell component 106A. The guide 426 can be integrated into or attached to the lateral support 404B. As seen, the guide 426 can define linear and/or curved pathways that direct the tensioning elements 420 between the tensioning unit 418 and the guides 428A, 428B on the medial shell component 106A.

In an embodiment, the tensioning elements 420 include a first tensioning element 420A forming a first loop over a distal posterior region of a lateral aspect of the socket system 400, a second tensioning element 420B forming a second loop over a distal anterior region of the lateral aspect, a third tensioning element 420C forming a third loop over a proximal anterior region of the lateral aspect, and a fourth tensioning element 420D forming a fourth loop over a proximal posterior region of the lateral aspect. Increasing tension in the tensioning elements 420A, 420B, 420C, and 420D reduces the circumferences of the loops, which, in turn, pulls the leading edges 430 of the medial shell component 406B together around a lateral shell component 406A, tightening the fit of the socket system 400 on the residual limb. The tensioning elements 420 are described as forming loops but can be routed in any suitable configuration.

Each tensioning element 420A, 420B, 420C, 420D extends between at least one control point 436 and a movable connection point 438 on a handle 432 of the tensioning unit 418. The at least one control point 436 can comprise the guide 426 or any other suitable point along the respective tensioning element between the shell components 406 and the tensioning unit 418. The handle 432 defines a moment arm rotatable about a rotation axis 434 and is operatively coupled to the tensioning elements 420. The rotation axis 434 is defined by a mounting bracket 490 mounting the handle 432 to the lateral support 404B. Like in other embodiments, the socket system 400 can be easily opened and closed with a simple manipulation of the tensioning unit 418 between on and off positions. In the off position (shown in FIG. 10A), slack or lower tension levels in the tensioning elements 420 can allow the system to move toward the open configuration.

In the on position (shown in FIG. 10B), the handle 432 effectively pulls and/or shortens the length of the tensioning elements 420 forming the loops, which, in turn, tensions the tensioning elements 420 and the shell components 406 to move the socket system 400 to the closed configuration. More particularly, movement of the handle 432 from the off position to the on position shifts the movable connection point 438 away from the control point 436 which, in turn, displaces the tensioning elements 420 up or down along the longitudinal axis 416. This tensions the tensioning elements 420 and the shell components 406 to move the socket system 400 to the closed configuration. The tensioning unit 418 can be binary so that a user can only lock the handle 432 in the on position or the off position, providing an intuitive and simple manner for users with limited dexterity or cognition to don and doff the socket system 400. The binary configuration of the tensioning unit 418 also decreases and/or eliminates the likelihood that a user will over-tighten and/or under-tighten the socket system 400 on the residual limb, enhancing safety and comfort. According to a variation, the binary configuration of tensioning unit 418 permits the user to only lock the handle 432 in the on position.

Figures 10A, 10B:
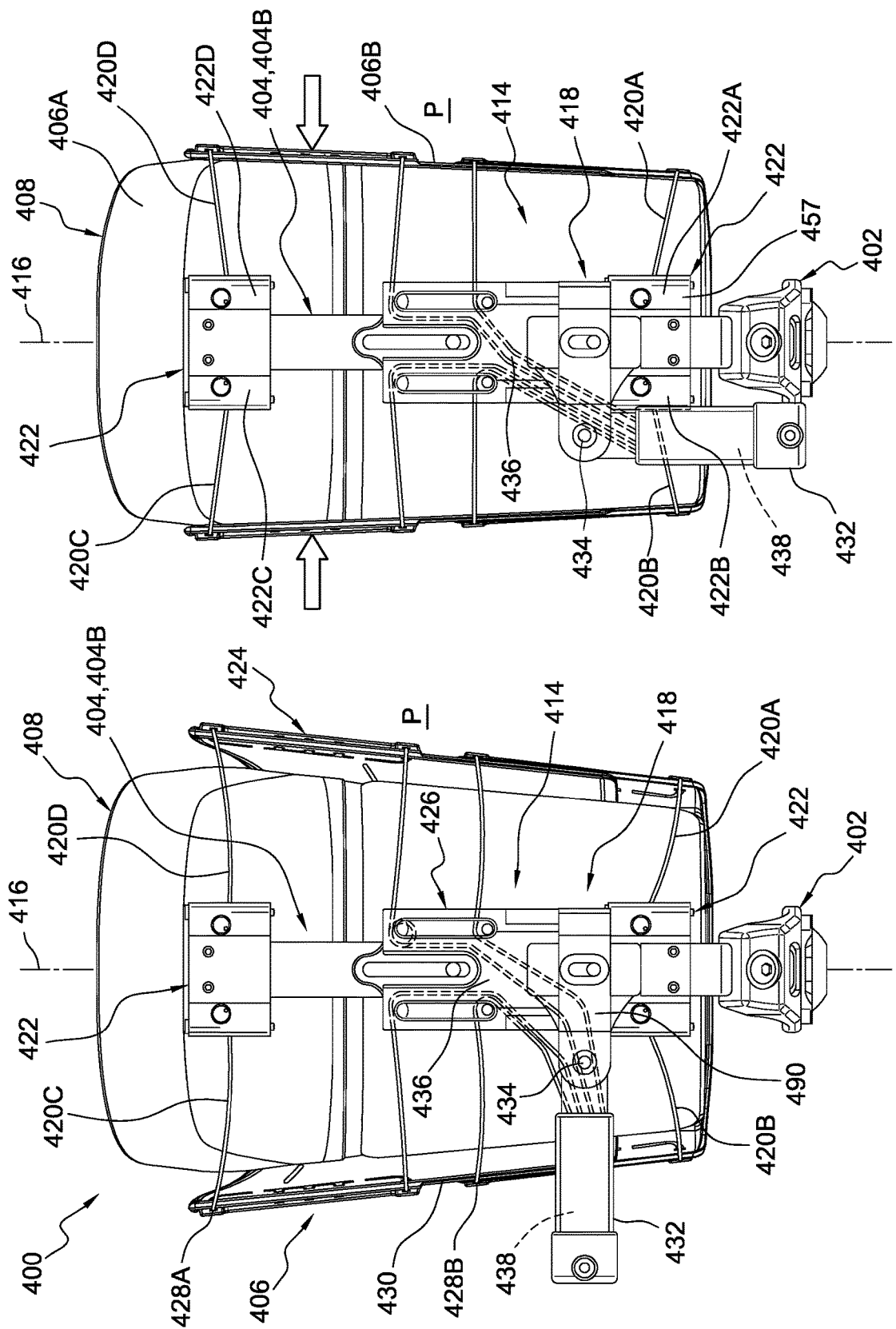
FIG. 10A is a side view of an adjustable socket system in an open configuration according to another embodiment.
FIG. 10B is side view of the adjustable socket system in FIG. 10A in a closed configuration.

According to a variation, the tightening system 414 provides a closing effect on the handle 432. For instance, the location of the tensioning elements 420A, 420B, 420C, 420D extending between the movable connection point 438 and the control point 436 is posterior to a longitudinal axis of the handle 432 when the handle 432 is in the on position as seen in FIG. 10B. This pulls the handle 432 in a closing or posterior direction P when the handle 432 moves toward the on position, providing a closing effect on the handle 432. This beneficially helps ensure that the handle 432 enters the on position and decreases the likelihood that the handle 432 will be accidentally dislodged due to impact from external objects. It also beneficially decreases the physical effort of putting the handle into the on position.

Referring to FIGS. 11A and 11B, the amount of displacement generated by the tensioner unit 418 can be varied by controlling one or more geometric relationships between the handle 432, the tensioning elements 420, and/or the mounting bracket 490. FIG. 11A schematically shows the handle 432 in the off position and FIG. 11B schematically shows the handle 432 in the on position.

The ability of the tensioner unit 418 to displace the tensioning elements 420 can be at least in part dependent on a distance L1 defined between the rotation axis 434 and the control point 436 or guide 426, a distance L2 defined between the rotation axis 434 and the movable connection point 438, a distance L3 defined between the rotation axis 434 and a free end of the handle 432, and an angle B defined between the horizontal and the handle 432. For example, an increase in the angle B can increase the amount of displacement of the tensioning elements 420. An increase of the ratio between L3 and L2 can increase mechanical advantage for a user. The amount of displacement of the tensioning elements 420 can tend to increase when L1 increases. An increase of L1 tends to cause the amount of displacement of the tensioning element 420 to depend more on L2.

Referring again to FIGS. 10A and 10B, the secondary tensioners 422 provide adjustment or control of tension in the tensioning elements 420 independent of the tensioning unit 418. For example, when the tensioning unit 418 is in the on position and the socket system 400 is in the closed configuration, a CPO can manipulate at least one of the secondary tensioners 422 to fine tune the fit or loading of the socket system 400 on the residual limb. The secondary tensioners 422 can comprise a first secondary tensioner 422A connected to the first tensioning element 420A, a second secondary tensioner 422B connected to the second tensioning element 420B, a third secondary tensioner 422C connected to the third tensioning element 420C, and a fourth secondary tensioner 422D connected to the fourth tensioning element 420D.

The secondary tensioners 422 are thus connected to different tensioning elements 420, which, in turn, allows the loading or fit of the socket system 400 to be proportionally or differentially adjusted. For example, the first and second secondary tensioners 422A, 422B and the third and fourth secondary tensioners 422C, 422D can be operable independent from one another such that a distal region of the socket system 400 can be controlled or adjusted independent of a proximal region of the socket system 400. In other embodiments, the third secondary tensioner 422C and the fourth secondary tensioner 422D can be operable independent from one another such that a proximal anterior region of the socket system 400 can be controlled or adjusted independent of a proximal posterior region of the socket system 400. The secondary tensioners 422 thus allow for fine tuning and localized adjustments of the socket system 400 when it is loaded or in the open configuration.

In the illustrated embodiment, the secondary tensioners 422 are worm-gear units. Referring to FIG. 12, each worm gear unit 422 can include a spool 451 having a worm wheel 453 arranged to mesh with an elongate worm member 455 located within a housing 457 (shown in FIG. 10B). A single tensioning element 420 can be attached to the spool 451 or two or more tensioning elements 420 can be attached to the spool 451.

In use, a CPO can use a tool to turn the worm member 455, which, in turn rotates the worm wheel 453 and spool 451. When the worm member 455 rotates in a tightening direction, the tensioning element 420 is drawn into the housing 457 and is wound around the spool 451. As the tensioning element 420 is wound around the spool 451, tension in the tensioning element 420 increases, causing the socket system 400 to tighten independent of the tensioning unit 418. When the worm member 455 rotates in a loosening direction, the tensioning element 420 unwinds from the spool 451 and at least part of the tensioning element 420 exits the housing 457. As the tensioning element 420 unwinds from the spool 451, tension in the tensioning element 420 decreases, loosening the socket system 400 independent from the tensioning unit 418. While the secondary tensioners 422 are described as worm gear units, in other embodiments the secondary tensioners 422 can comprise other dial tensioners or any other suitable mechanism.

The tensioning unit 418 may include at least one elastic element to permit automatic volume adjustment of the socket system 400. FIG. 13 schematically illustrates a volume adjustment system comprising an elastic element 474 located within a grip portion 432B of the handle 432 according to an embodiment. As described above, loading and unloading of the elastic element 474 by the tensioning elements 420 can deflect (e.g., shorten or elongate) the elastic element 474, which, in turn, can adapt or adjust the fit of the socket system 400 to better match the residual limb.

As seen, the elastic element 474 is positioned within a housing unit 433 and loaded between an end of the housing unit 433 and a loading member 494. The housing unit 433 is positioned within the grip portion 432B. The tensioning element 420 is connected to the loading member 494 and extends from the loading member 494 through a center of the elastic element 474 and out of the grip portion 432B via an opening in the end of the grip portion 432B. It will be appreciated that the housing unit 433 can be omitted and the elastic element 474 can be loaded within the grip portion 432B or located outside of the handle 432.

In use, when the tensioning element 420 is tensioned in a direction Y it forces the loading member 494 in the direction Y, loading the elastic element 474 between the loading member 494 and the end of the housing unit 433, which, in turn, deflects or shortens the elastic element 474. Within an elastic range of the elastic element 474, the amount of deflection or shortening of the elastic element 474 increases with the magnitude of load on the elastic element 474. Like in other embodiments, this shortening effectively increases the length of the tensioning element 420 outside of the grip portion 432B, allowing for an increased circumference of the socket system 400 when the socket system 400 enters the closed configuration. This allows the socket system 400 to more comfortably fit residual limbs of different sizes and automatically adjust the volume of the socket system 100 to match that of the residual limb.

Optionally, the tensioning unit 418 can include a lockout system that fixes the length of the elastic element 474 once the tensioning unit 418 is in the on position. This makes it so that the elastic element 474 cannot deflect when locked out, which, in turn prevents the elastic element 474 from varying the volume of the socket system 400 when the socket system 400 is in the closed configuration. In other embodiments, the elastic element 476 is arranged such that the input force required to move the handle 432 between the off and on positions is generally constant over the range of motion of the handle 432. For instance, the elastic element 474 can comprise a constant force spring.

In other embodiments, the tensioning elements 420A, 420B, 420C, 420D can be connected to four corresponding elastic or spring elements 474 within the grip portion 432B. This allows the fit or the forces applied to different regions of the residual limb by the tensioning elements 420 to be different when the tensioning unit 418 is in the on position. It will be appreciated that the elastic element 474 can comprise compression springs, constant force springs, pre-tension springs, variable tension springs, combinations thereof, or any other suitable elastic element.

Referring to FIG. 14, the grip portion 432B can include a feedback system for communicating an amount of tension present in the tensioning elements 420 or loads on the elastic element 474. For instance, the grip portion 432B can define an observation window 496 for visually observing loading of the elastic element 474. The grip portion 432B can include a series of indicators 498A, 498B, 498C located along the observation window 496. If the elastic element 474 is maximally loaded or compressed, the loading member 494 can substantially align with the indicator 498A, alerting the user or clinician that volume adaption of the tensioning unit 418 is exceeded and that the socket system 400 no longer fits safely.

If the elastic element 474 is minimally loaded or compressed, the loading member 494 can substantially align with the indicator 498C. If loading or compression of the elastic element 474 is between the maximum and minimal loading, the loading member 494 can substantially align with indicators 498B. The tightening system 414 can thus communicate to the user almost immediately how much tension is present in the tensioning elements or how much volume adaptation is occurring, improving user comfort and safe use. In other embodiments, the user can observe via the observation window 496 either of two differently colored regions. One color indicates that volume adaption of the tensioning unit 418 is exceeded and that the socket system 400 no longer fits safely. The other color indicates that the volume adaption of the tensioning unit 418 is in a safe range.

It will be appreciated that while the elastic element 474 is described as being carried within the grip portion 432B, the elastic element 474 can be carried within any structure, such as on one of the longitudinal supports 404. Moreover, while the tightening system 414 is generally described on the lateral aspect of the socket system 400, the tightening system 414 can be adapted for use on the medial, anterior, or posterior aspect of the socket system 400 to achieve the same or similar benefits.

FIGS. 15A and 15B illustrate a tensioning unit 518 according to another embodiment including a force mechanism 501 that can be adapted for use with different adjustable socket embodiments of the present disclosure. The force mechanism 501 is arranged such that the input force required to move the tensioning unit 518 between the off and on positions is substantially constant. The force mechanism 501 can be incorporated in the handle or can be located near the handle.

In an embodiment, the force mechanism 501 includes a first pulley 503 and a second pulley 505. The first pulley 503 can be larger than the second pulley 505. A first elongate element 507 is wound around the first pulley 503 and a second elongate element 509 is wound around the second pulley 505. An elastic or spring element 511 attaches an end of the second elongate element 509 to an anchor point 513. The second pulley 505 is fixed in position relative to the first pulley 503 and is offset from a center 515 of the first pulley 503.

When the first and second pulleys 503, 505 are rotated in a first direction via the first elongate element 507 or a handle of the present disclosure, the second elongate element 509 is wound onto the second pulley 505. This winding of the second elongate element 509 extends the spring element 511. The force in the spring element 511 linearly increases with its extension. A distance from a periphery of the second pulley 505 when the first elongate element 507 is tangent decreases when the pulleys 503, 505 are rotated in the first direction. This counters the increasing tension-force in the spring element 511, resulting in a substantially constant required force to rotate the first pulley 503 or move a tensioning unit 518 between the on and off positions via the constant force mechanism 501.

FIG. 16 illustrates a tensioning unit according to another embodiment including a force mechanism 601. It will be appreciated that the force mechanism 601 can be adapted for use with any the embodiments described herein. The force mechanism 601 includes a pulley assembly 603 loaded onto a bearing 605 by a spring member 607 and defining a winding surface 609. The compression force from the spring member 607 can be adjusted by manipulating an adjustment screw 611.

The pulley assembly 603 is arranged to rotate freely on the bearing 605 in a first direction and only to rotate on the bearing 605 in a second direction opposite the first direction when the applied torque overcomes frictional forces acting on the pulley assembly 603 due to the compression from the spring member 607. This allows an elongate element 619 to be unwound from the winding surface 609 with a constant force. A gear member 613 carries an elastic element and defines a first plurality of teeth 615 interacting with a second plurality of teeth 617 on the pulley assembly 603. The elastic element can comprise a clock spring or any other suitable elastic element.

When the pulley assembly 603 is rotated by pulling the elongate element 619 or via a handle attached to the pulley assembly 603, the interaction between the teeth 615, 617 rotates the gear member 613, which, in turn, winds or loads the elastic element of the gear member 613. When the force in the elongate element 619 is released or reduced enough the spring in the gear member 613 can unwind and rotate the pulley assembly 603 in the first direction, pulling the elongate element 619 back onto the winding surface 609. This results in a substantially constant required force to rotate the pulley assembly 603 or move the tensioning unit between the on and off positions.

FIG. 17 illustrates an adjustable socket system 700 according to yet another embodiment. The socket system 700 is similar to other embodiments of the present disclosure including a base 702 arranged to provide support for a distal end of a residual limb, a plurality of longitudinal supports 704 connected to the base 702, and a plurality of shell components 706 operatively connected to the supports 704. The shell components 706 including a medial shell component 706A and lateral shell component 706B, collectively forming a socket wall 708 defining a receiving volume adapted to receive the residual limb.

Like in other embodiments, a tightening system 714 is arranged to move the socket system 700 between open and closed configurations and includes a tensioning unit 718, one or more tensioning elements 720 operatively coupled to the tensioning unit 718, and one or more secondary tensioners 722 operatively coupled to the tensioning elements 720. The tensioning elements 720 are routed through a plurality of guides 724 on the shell components 706 and/or the supports 704 and may be formed of line, cord, wire, string, combinations thereof, or any other suitable element.

The guides 724 can include upper and lower guides 728A, 728B that form first and second loops with the tensioning elements 720 over the lateral aspect of the socket system 700. A first tensioning element 720A forms a first loop over a distal region of the lateral aspect of the socket system 700, and a second tensioning element 720B forms a second loop over a proximal region of the lateral aspect of the socket system 700. Increasing tension in the first tensioning element 720A and second tensioning element 720B reduces the circumference of the loops, which, in turn, pulls the leading edges 730 of the medial shell component 706B together, tightening the fit of the socket system 700. While the tensioning elements 720 are described forming loops it will be appreciated that the tensioning elements 720 can be routed on the socket system 700 in any suitable configuration and on any suitable region.

The tensioning unit 718 includes a handle 732 defining a moment arm rotatable about a rotation axis 734 and operatively coupled to the tensioning elements 720. The handle 732 is movable between an off position and an on position in which the handle 732 is orientated generally parallel to the lateral support 704A. In the off position, slack can be present in the tensioning elements 720 so that the socket system 700 can move toward the open configuration.

In the on position, the handle 732 effectively pulls and/or shortens the length of the tensioning elements 720 forming the loops, which, in turn, tensions the tensioning elements 720 and shell members 706 to move the socket system 700 to the closed configuration. More particularly, the tensioning elements 720 on the tensioning unit 718 extend between at least one control point 736 directing the tensioning elements 720 between the tensioning unit 718 and the medial shell component 706A and at least one movable connection point 738 on the handle 732. The at least one control point 736 can be defined on the lateral support 704B or any other suitable point along the tensioning elements between the shell components 706 and the tensioning unit 718.

Rotation of the handle 732 from the off position to the on position, shifts the movable connection point 738 away from the at least one control point 736 in a direction along the longitudinal axis 716, which, in turn, displaces the tensioning elements 720 downwardly along the longitudinal axis 716. This displacement tensions the tensioning elements 720 and the shell components 706 to move the socket system 700 to the closed configuration.

The tensioning unit 718 can be binary such that it can only be locked or placed in the on position or the off position. The binary configuration of the tensioning unit 718 decreases and/or eliminates the likelihood that a user will over-tighten and/or under-tighten the socket system 700 on the residual limb, enhancing safety and comfort. This beneficially improves ease of use for the socket system 700, especially for elderly users. According to a variation, the binary configuration of tensioning unit 718 permits the user to only lock the handle 732 in the on position.

In addition, the elongate configuration of the handle 732 provide a mechanical advantage and large gripping portion for the user, facilitating operation of the tensioning unit 718 for users with limited to little dexterity. Optionally, the tensioning unit 718 can include at least one elastic element connected to the tensioning elements 720 and arranged to permit automatic volume adjustment of the socket system 700. In other embodiments, the elastic element can be arranged so that the input force required to move the handle 732 between the on and off positions is generally constant over the range of motion of the handle 732.

Secondary tensioners 722 are located on the handle 732 and enable tension control of the tensioning elements 720 independent of the tensioning unit 718. When the handle 732 is in the on position, the user or CPO can manipulate at least one of the secondary tensioners 722 to fine tune the fit or loading of the socket system 700 on the residual limb. The secondary tensioners 722 can include a first secondary tensioner 722A connected to the first tensioning element 720A and a second secondary tensioner 722B connected to the second tensioning element 720B. The loading or fit of the socket system 700 can thus be proportionally or differentially adjusted using the secondary tensioners 722. For instance, the secondary tensioners 722 can be operably independent from one another such that the proximal area of the socket system 700 can be controlled or adjusted independent of the distal area of the socket system 700.

In addition, the secondary tensioners 722 define the at least one movable connection point 738, simplifying the design of the tensioning unit 718. The secondary tensioners 722 can be a geared mechanism or any other suitable tensioning mechanism.

It will be appreciated that the embodiments described herein are to be regarded as exemplary only, as any adjustable socket system is possible. The features of one adjustable socket system embodiment can be combined or adapted for use with another adjustable socket system embodiment. For instance, the tensioning unit 118 can be arranged to include a volume adjustment system comprising one or more elastic elements.

Figure 18B:
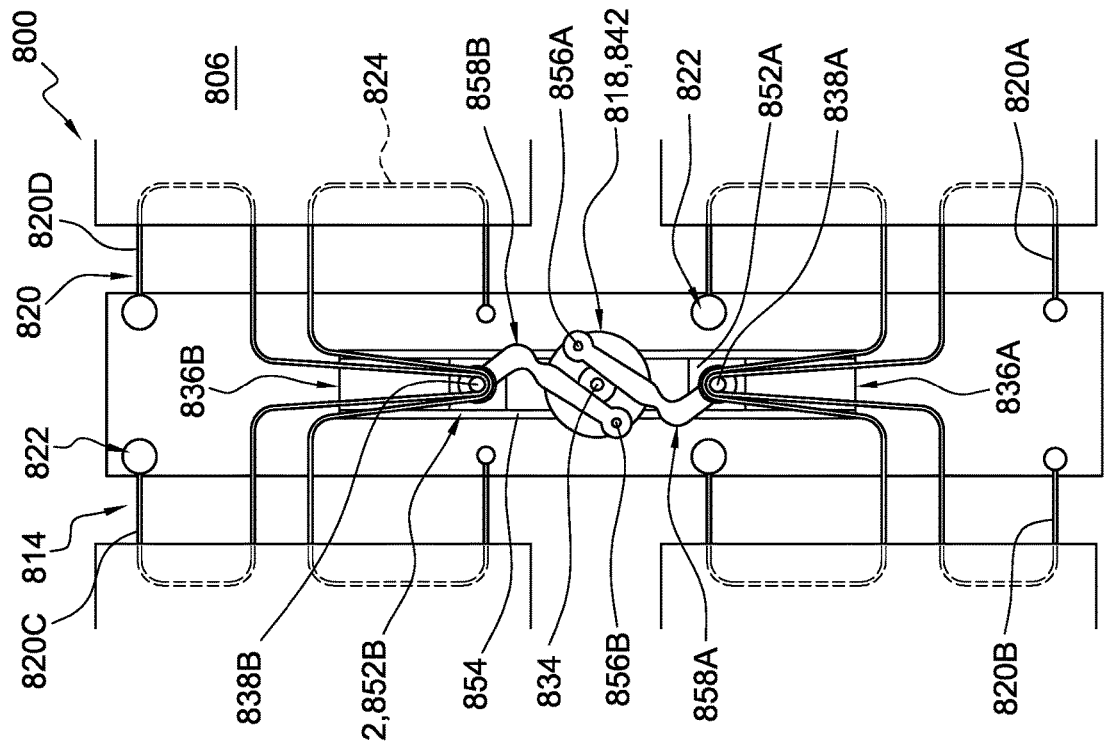
FIG. 18B is a partial schematic view of the tensioning unit of FIG. 18A in an on position according to an embodiment.
Figure 18A:
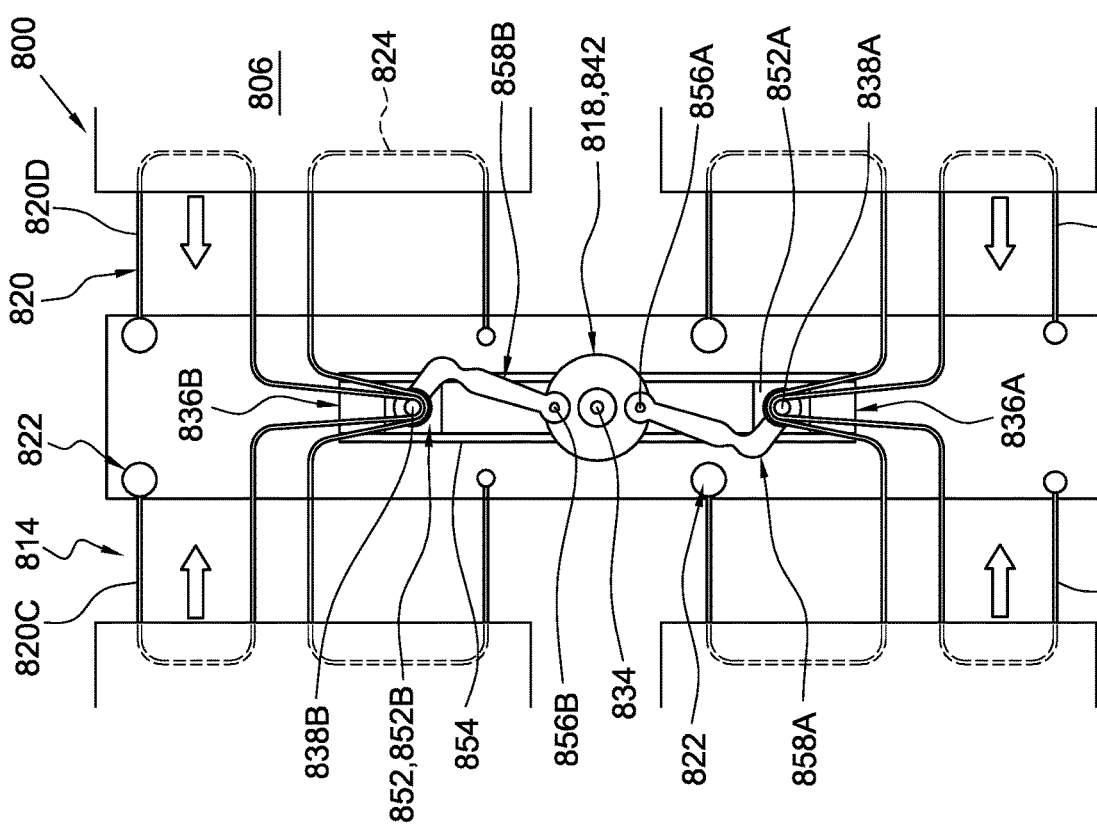
FIG. 18A is a partial schematic view of a tightening system with a tensioning unit in an off position according to an embodiment.

FIGS. 18A and 18B are schematic views of a tightening system 814 for use with an adjustable socket system 800 movable between open and closed configurations according to yet another embodiment. The tightening system 814 is similar to other embodiments including a tensioning unit 818, one or more tensioning elements 820 arranged to interact with the tensioning unit 818, and one or more secondary tensioners 822 operatively coupled to the tensioning elements 820. The tensioning elements 820 are routed through a plurality of guides 824 on a shell component 806 of the adjustable socket system 800. Each tensioning element 820 includes an end attached to a corresponding secondary tensioner 822 and interacts with at least one movable connection point 838.

The tensioning unit 818 is movable between on and off positions and includes a displacement wheel 842 that is rotatable about a rotation axis 834 via a handle (see, e.g., handle 132 shown in FIGS. 2A and 2B) defining a moment arm or other actuator.

The displacement wheel 842 defines a first location point 856A and a second location point 856B that move along a circular path about the rotation axis 834. The least one slide member 852 is slidably attached to a track 854 on a support base 868. It will be appreciated that the support base 868 can be attached to or integrated into a longitudinal support or shell component of the adjustable socket system 800.

The at least one slide member 852 includes first and second slide members 852A, 852B comprising first and second movable connection points 838A, 838B that interact with the tensioning elements 820. For instance, the tensioning elements 820 can include first and second tensioning elements 820A, 820B having one or more segments extending between the first slide member 852A and a first control point 836A, and third and fourth tensioning elements 820C, 820D having one or more segments extending between the second slide member 852B and a second control point 836B.

A first linking member 858A connects the first slide member 852A to the first location point 856A on the displacement wheel 842 and a second linking member 858B can connect the second slide member 852B to the second location point 856B on the displacement wheel 842. The first and second linking members 858A, 858B can be eccentrically attached to the displacement wheel 842. The first and second linking members 858A, 858B can pivot around the connection between the first and second linking members 858A, 858B and the slide members 852A, 852B and/or the connection between the first and second linking members 858A, 858B and the displacement wheel 842. The linking members 858A, 858B are shown forming an angle but can have any shape suitable to convert rotational movement of the displacement wheel 842 into translational movement of the slide members 852A, 852B.

In the off position (shown in FIG. 18A), tension levels or slack in the tensioning elements 820 can permit the socket system 800 to move toward the open configuration. The engagement or interaction between the tensioning elements 820 and the slide members 852A, 852B is such that movement of the handle from the off position to the on position (shown in FIG. 18B) displaces the linking members 858A, 858B up or down relative to the first and second control points 836A, 836B, which, in turn, drives the slide members 852A, 852B up or down along the track 854. The movement of the slide members 852A, 852B along the track 854 displaces the tensioning elements 820 up or down relative to the first and second control points 836A, 836B, which, in turn, tensions the tensioning elements 820 and the shell components 806 to move the adjustable socket system 800 to the closed configuration.

The tensioning unit 818 can be binary such that it can only be locked or placed in the on position or the off position. The binary configuration of the tensioning unit 818 decreases and/or eliminates the likelihood that a user will over-tighten or under-tighten the socket system 800 on the residual limb, enhancing safety and comfort. According to a variation, the binary configuration of the tensioning unit 818 permits the user to only lock the handle in the on position.

In other embodiments, the adjustable socket system of the present disclosure can be assembled from components selected from groups of components that include shell members, struts, distal assemblies, and/or suspension systems. The components within these groups are modular, meaning that they vary in size and shape but have common connecting features. This modularity applies to assembling and also repair or reconfiguration of the assembled system, by simply switching components in and out.

In other embodiments, the longitudinal supports can comprise struts and/or the longitudinal supports can include three, four, or any other suitable number of supports. In other embodiments, the adjustable socket system can include anterior and posterior longitudinal supports. In other embodiments, the shell components can be omitted and the tensioning unit can be operatively coupled to the longitudinal supports to move the system between the open and closed configuration. In yet other embodiments, the longitudinal supports can be omitted and the tensioning unit can be operatively coupled to the shell components to move the system between the open and closed configuration.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. An adjustable socket system comprising:
    a base;
    a plurality of longitudinal supports connected to the base and extending along a longitudinal axis of the adjustable socket system;
    a plurality of shell components operatively connected to the plurality of longitudinal supports and at least in part defining a receiving volume adapted to receive a residual limb, the adjustable socket system movable between an open configuration in which at least some of the plurality of shell components are moved radially outward relative to the longitudinal axis to loosen a fit of the adjustable socket system, and a closed configuration in which at least some of the plurality of shell components are moved radially inward relative to the open configuration to secure the fit of the adjustable socket system on the residual limb; and a tightening system arranged to selectively move the adjustable socket system between the open and closed configurations, the tightening system comprising:

a tensioning unit including at least one movable connection point and a handle defining a moment arm rotatable about a rotation axis, the handle having an elongate connecting portion and a grip portion extending from a first end of the elongate connecting portion and toward the plurality of shell components, a second end of the elongate connecting portion located at the rotation axis; and at least one tensioning element operatively coupled to the handle via the at least one movable connection point and to at least one of the plurality of shell components via at least one control point, wherein rotation of the handle about the rotation axis from an off position to an on position displaces both of the at least one movable connection point and the at least one tensioning element relative to the at least one control point to tension the at least one tensioning element and to move the adjustable socket system to the closed configuration;

wherein the at least one movable connection point is located on a displacement wheel coupled to one of the plurality of longitudinal supports and rotatable by the handle, the at least one movable connection point comprises a pulley assembly attached to the displacement wheel and engaging the at least one tensioning element;

wherein the handle has a binary configuration such that the handle is only positionable in the on position or the off position.

2. The adjustable socket system of claim 1, wherein the at least one tensioning element includes a first tensioning element and a second tensioning element, and wherein the at least one movable connection point comprises a first pulley assembly attached to the displacement wheel and engaging the first tensioning element and a second pulley assembly attached to the displacement wheel and engaging the second tensioning element.

3. The adjustable socket system of claim 2, wherein the first and second pulley assemblies are radially offset relative to the longitudinal axis.

4. The adjustable socket system of claim 2, wherein the first and second pulley assemblies are angularly offset relative to one another on the displacement wheel.

5. The adjustable socket system of claim 1, wherein the at least one tensioning element is operatively coupled to the handle via at least one elastic element.

6. The adjustable socket system of claim 5, wherein deflection of the at least one elastic element permits radial adjustment of at least one of the plurality of shell components.

7. The adjustable socket system of claim 5, wherein the at least one tensioning element comprises a first tensioning element on a distal aspect of the adjustable socket system and a second tensioning element on a proximal aspect of the adjustable socket system, and wherein the at least one elastic element includes a first elastic element attached to the first tensioning element and a second elastic element attached to the second tensioning element.

8. The adjustable socket system of claim 1, wherein the plurality of shell components includes a medial shell component and the handle wraps around an anterior aspect of the medial shell component near the base.

9. The adjustable socket system of claim 1, wherein the handle is only lockable in the on position.

10. The adjustable socket system of claim 9, wherein the grip portion extends generally perpendicular from the elongate connecting portion.

11. The adjustable socket system of claim 1, wherein the tightening system includes at least one secondary tensioner arranged to adjust tension in the at least one tensioning element independent of the tensioning unit.

12. The adjustable socket system of claim 1, wherein the at least one movable connection point is located inside of the grip portion of the handle.

13. The adjustable socket system of claim 1, wherein rotation of the handle in the on position displaces the grip portion adjacent the base and below the plurality of shell components.

14. An adjustable socket system comprising:

a base;

a plurality of longitudinal supports connected to the base and extending along a longitudinal axis of the adjustable socket system;

a plurality of shell components operatively connected to the plurality of longitudinal supports and at least in part defining a receiving volume adapted to receive a residual limb, the adjustable socket system movable between an open configuration in which at least some of the plurality of shell components are moved radially outward relative to the longitudinal axis to loosen a fit of the adjustable socket system, and a closed configuration in which at least some of the plurality of shell components are moved radially inward relative to the open configuration to secure the fit of the adjustable socket system on the residual limb; and a tightening system arranged to selectively move the adjustable socket system between the open and closed configurations, the tightening system comprising:

a tensioning unit including a displacement wheel, at least one pulley assembly, and a handle defining a moment arm for rotating the displacement wheel about a rotation axis, the handle having an elongate connecting portion and a grip portion extending from a first end of the elongate connecting portion and toward of the plurality of shell components, a second end of the elongate connecting portion located at the rotation axis; and at least one tensioning element operatively coupled to the handle via an engagement with the at least one pulley assembly on the displacement wheel and to at least one of the plurality of shell components via at least one control point, wherein rotation of the handle from an off position to an on position displaces both of the at least one pulley assembly and the at least one tensioning element relative to the at least one control point to tension the at least one tensioning element and to move the adjustable socket system to the closed configuration;

wherein the handle has a binary configuration such that the handle is only positionable in the on position or the off position.

15. The adjustable socket system of claim 14, wherein the at least one control point is defined at least in part by a guide arranged to direct the at least one tensioning element between the tensioning unit and the at least one of the plurality of shell components.

16. The adjustable socket system of claim 15, wherein the guide is mounted on a lateral support of the plurality of longitudinal supports.

* * * * *